United States Patent
Mesaeli

(12) 
(10) Patent No.: US 7,186,882 B2
(45) Date of Patent: Mar. 6, 2007

(54) TRANSGENIC MOUSE OVER-EXPRESSING CALRETICULIN (CRT) IN VASCULAR SMOOTH MUSCLE CELLS

(76) Inventor: Nasrin Mesaeli, 351 Tache Avenue, Winnipeg Manitoba (CA) R2H 2A6

( * ) Notice: Subject to any disclaimer, the term of this patent is extended or adjusted under 35 U.S.C. 154(b) by 0 days.

(21) Appl. No.: 10/803,095

(22) Filed: Mar. 18, 2004

(65) Prior Publication Data

US 2004/0205837 A1    Oct. 14, 2004

Related U.S. Application Data

(60) Provisional application No. 60/455,399, filed on Mar. 18, 2003.

(51) Int. Cl.
| | |
|---|---|
| A01K 67/00 | (2006.01) |
| A01K 67/027 | (2006.01) |
| C12N 15/00 | (2006.01) |
| C07H 21/02 | (2006.01) |
| C07H 21/04 | (2006.01) |

(52) U.S. Cl. .................. 800/18; 800/8; 800/9; 800/13; 800/25; 536/23.1

(58) Field of Classification Search ............... 536/23.1; 435/325; 800/9, 18, 21, 8, 13, 25
See application file for complete search history.

(56) References Cited

OTHER PUBLICATIONS

Goswami et al. (2003, Journal of Molecular Evolution, 57:44-51).*
Cowan et al., (2003, Xenotransplantation, 10: 223-231).*
Li et al. (1996, Journal of Cell Biology, 132: 849-859).*
Hammer et al., (1990, Cell: 63: 1099-1112).*
Nakamura et al. (2001, J. of Clinical Investigation, 107:1245-1253).*
Dai et al. (1997, Arterioscler Thromb Vasc Biol, 17:2359-2368).*
Soloway et al., 1995, JBC, 270: 13460-13469.*
Michalak et al., 1999, Biochem J. 344: 281-292.*

* cited by examiner

*Primary Examiner*—Anne M. Wehbé
*Assistant Examiner*—Joanne Hama
(74) *Attorney, Agent, or Firm*—Michael R. Williams; Adrian D. Battison; Ryan W. Dupuis

(57) ABSTRACT

A transgenic mouse whose genome comprises a transcriptional control region operably linked to a cDNA encoding calreticulin (CRT) is described.

7 Claims, 17 Drawing Sheets

A

B

A. Wild Type
B. *SMCRT*

Figure 16
Nucleotide and protein sequence of SM22α–CRT

```
CCCCTTCCTT CAGATGCCAC AAGGAGGTGC TGGAGTTCTA TGCACCAATA GCTTAAACCA GCCAGGCTGG CTGTAGTGGA
TTGAGCGTCT GAGGCTGCAC CTCTCTGGCC TGCAGCCAGT TCCTGGGTGA GACTGACCCT GCCTGAGGGT TCTCTCCTTC
CCTCTCTCTA CTCCTTTCCT CCCTCTCCCT CTCCCTCTCT CTGTTTCCTG AGGTTTCCAG GATTGGGGAT GGGACTCAGA
GACACCACTA AAGCCTTACC TTTTAAGAAG TTGCATTCAG TGAGTGTGTG AGACATAGCA CAGATAGGGG CAGAGGAGAG
CTGGTTCTGT CTCCACTGTG TTTGGTCTTG GGTACTGAAC TCAGACCATC AGGTGTGATA GCAGTTGTCT TTAACCCTAA
CCCTGAGCCT GTCTCACCTG TCCCTTCCCA AGACCACTGA AGCTAGGTGC AAGATAAGTG GGGACCCTTT CTGAGGTGGT
AGGATCTTTC ACGATAAGGA CTATTTTGAA GGGAGGGAGG GTGACACTGT CCTAGTCCTC TTACCCTAGT GTCCTCCAGC
CTTGCCAGGC CTTAAACATC CGCCCATTGT CACCGCTCTA GAAGGGGCCA GGGTTGACTT GCTGCTAAAC AAGGCACTCC
CTAGAGAAGC ACCCGCTAGA AGCATACCAT ACCTGTGGGC AGGATGACCC ATGTTCTGCC ACGCACTTGG TAGCCTTGGA
AAGGCCACTT TGAACCTCAA TTTTCTCAAC TGTTAAATGG GGTGGTAACT GCTATCTCAT AATAAAGGGG AACGTGAAAG
GAAGGCGTTT GCATAGTGCC TGGTTGTGCA GCCAGGCTGC AGTCAAGACT AGTTCCCACC AACTCGATTT TAAAGCCTTG
CAAGAAGGTG GCTTGTTTGT CCCTTGCAGG TTCCTTTGTC GGGCCAAACT CTAGAATGCC TCCCCCTTTC TTTCTCATTG
AAGAGCAGAC CCAAGTCCGG GTAACAAGGA AGGGTTTCAG GGTCCTGCCC ATAAAAGGTT TTTCCCGGCC GCCCTCAGCA
CCGCCCCGCC CCGACCCCCG CAGCATCTCC AAAGCATGCA GAGAATGTCT CCGGCTGCCC CCGACAGACT GCTCCAACTT
GGTGTCTTTC CCCAAATATG GAGCCTGTGT GGAGTGAGTG GGGCGGCCCG GGTGGTGAG CCAAGCAGAC TTCCATGGGC
AGGGAGGGGC GCCAGCGGAC GGCAGAGGGG TGACATCACT GCCTAGGCGG CCTTTAAACC CCTCACCCAG CCGGCGCCCC
AGCCCGTCTG CCCCAGCCCA GACACCGAAG CTACTCTCCT TCCAGTCCAC AAACGACCAA GCCTTGtcga caagctTGGT
                                                                          start-ATG
ACCGAGCTCG GATCCACTAG TCCAGTGTGG TGGAATTCAT GCTGCTCCCT GTGCCGCTGC TGCTCGGCCT GCTCGGCCTG
                                           ▶Me tLeuLeuPro ValProLeuL euLeuGlyLe uLeuGlyLeu
GCCGCCGCCG AGCCCGTCGT CTACTTCAAG GAGCAGTTTC TGGACGGAGA TGGGTGGACC GAGCGCTGGA TCGAATCCAA
▶AlaAlaAlaG luProValVa lTyrPheLys GluGlnPheL euAspGlyAs pGlyTrpThr GluArgTrpI leGluSerLy
ACACAAGTCC GATTTTGGCA AATTCGTCCT CAGTTCGGGC AAGTTCTACG GCGATCAGGA GAAAGATAAA GGGCTGCAGA
▶sHisLysSer AspPheGlyL ysPheValLe uSerSerGly LysPheTyrG lyAspGlnGl uLysAspLys GlyLeuGlnT
CCAGCCAGGA CGCCCGCTTC TACGCCCTGT CGGCCCGATT CGAGCCGTTC AGCAACAAGG GCCAGCCACT GGTGGTGCAG
▶hrSerGlnAs pAlaArgPhe TyrAlaLeuS erAlaArgPh eGluProPhe SerAsnLysG lyGlnProLe uValValGln
TTCACCGTGA AACACGAGCA GAACATTGAC TGCGGGGGCG GCTACGTGAA GCTGTTTCCG GCCGGCCTGG ACCAGAAGGA
▶PheThrValL ysHisGluGl nAsnIleAsp CysGlyGlyG lyTyrValLy sLeuPhePro AlaGlyLeuA spGlnLysAs
CATGCACGGG GACTCTGAGT ACAACATCAT GTTTGGTCCT GACATCTGTG GCCCCGGCAC CAAGAAGGTT CACGTCATCT
▶pMetHisGly AspSerGluT yrAsnIleMe tPheGlyPro AspIleCysG lyProGlyTh rLysLysVal HisValIleP
TCAACTACAA GGGCAAGAAC GTGCTGATCA ACAAGGACAT CCGTTGCAAG GACGACGAGT TCACACACCT GTACACGCTG
▶heAsnTyrLy sGlyLysAsn ValLeuIleA snLysAspII eArgCysLys AspAspGluP heThrHisLe uTyrThrLeu
ATCGTGCGGC CGGACAACAC GTATGAGGTG AAGATTGACA ACAGCCAGGT GGAGTCGGGC TCCCTGGAGG ATGACTGGGA
▶IleValArgP roAspAsnTh rTyrGluVal LysIleAspA snSerGlnVa lGluSerGly SerLeuGluA spAspTrpAs
CTTCCTACCC CCCAAGAAGA TAAAGGACCC AGATGCCTCG AAGCCTGAAG ACTGGGACGA GCGGGCCAAG ATCGACGACC
▶pPheLeuPro ProLysLysI leLysAspPr oAspAlaSer LysProGluA spTrpAspGl uArgAlaLys IleAspAspP
CCACGGACTC CAAGCCCGAG GACTGGGACA AGCCCGAGCA CATCCCCGAC CCGGACGCGA AGAAGCCCGA AGACTGGGAC
▶roThrAspSe rLysProGlu AspTrpAspL ysProGluHi sIleProAsp ProAspAlaL ysLysProGl uAspTrpAsp
GAAGAAATGC ACGGAGAGTG GGAGCCGCCG GTGATTCAGA ACCCCGAGTA CAAGGGTGAG TGGAAGCCGC GGCAGATCGA
▶GluGluMetA spGlyGluTr pGluProPro ValIleGlnA snProGluTy rLysGlyGlu TrpLysProA rgGlnIleAs
CAACCCCGAT TACAAAGGCA CCTGGATCCA CCCCGAAATC GACAACCCCG AGTACTCGCC CGACGCTAAC ATCTATGCCT
▶pAsnProAsp TyrLysGlyT hrTrpIleHi sProGluIle AspAsnProG luTyrSerPr oAspAlaAsn IleTyrAlaT
ACGACAGCTT TGCCGTGCTG GGCTTGGACC TCTGGCAGGT CAAGTCGGGC ACCATCTTCG ACAACTTCCT CATCACCAAC
▶yrAspSerPh eAlaValLeu GlyLeuAspL euTrpGlnVa lLysSerGly ThrIlePheA spAsnPheLe ulleThrAsn
GATGAGGCGT ACGCAGGAGA GTTTGGCAAC GAGACGTGGG GCGTCACCAA GACGGCCGAG AAGCAGATGA AAGACAAGCA
▶AspGluAlaT yrAlaGluGl uPheGlyAsn GluThrTrpG lyValThrLy sThrAlaGlu LysGlnMetL ysAspLysGl
GGACGAGGAG CAGCGGCTGA AGGAGGAGGA GGAGGAGAAG AAGCGGAAGG AGGAGGAGGA GGCCGAGGAG GACGAGGAGG
▶nAspGluGlu GlnArgLeuL ysGluGluGl uGluGluLys LysArgLysG luGluGluGl uAlaGluGlu AspGluGluA
ACAAGGACGA CAAGGAGGAC GAGGATGAGG ACGAGGAGGA CAAGGACGAG GAGGAGGAGG AGGCGGCCGC CGGCCAGGCC
▶spLysAspAs pLysGluAsp GluAspGluA spGluGluAs pLysAspGlu GluGluGluG luAlaAlaAl aGlyGlnAla
AAGGACGAGC TGTAG
▶LysAspGluL eu···
```

Figure 17
Nucleotide and protein sequence of SM22α–CRT–HA

```
CCCCTTCCTT CAGATGCCAC AAGGAGGTGC TGGAGTTCTA TGCACCAATA GCTTAAACCA GCCAGGCTGG CTGTAGTGGA
TTGAGCGTCT GAGGCTGCAC CTCTCTGGCC TGCAGCCAGT TCCTGGGTGA GACTGACCCT GCCTGAGGGT TCTCTCCTTC
CCTCTCTCTA CTCCTTTCCT CCCTCTCCCT CTCCCTCTCT CTGTTTCCTG AGGTTTCCAG GATTGGGGAT GGGACTCAGA
GACACCACTA AAGCCTTACC TTTTAAGAAG TTGCATTCAG TGAGTGTGTG AGACATAGCA CAGATAGGGG CAGAGGAGAG
CTGGTTCTGT CTCCACTGTG TTTGGTCTTG GGTACTGAAC TCAGACCATC AGGTGTGATA GCAGTTGTCT TTAACCCTAA
CCCTGAGCCT GTCTCACCTG TCCCTTCCCA AGACCACTGA AGCTAGGTGC AAGATAAGTG GGACCCTTT CTGAGGTGGT
AGGATCTTTC ACGATAAGGA CTATTTTGAA GGGAGGGAGG GTGACACTGT CCTAGTCCTC TTACCCTAGT GTCCTCCAGC
CTTGCCAGGC CTTAAACATC CGCCCATTGT CACCGCTCTA GAAGGGGCCA GGGTTGACTT GCTGCTAAAC AAGGCACTCC
CTAGAGAAGC ACCCGCTAGA AGCATACCAT ACCTGTGGGC AGGATGACCC ATGTTCTGCC ACGCACTTGG TAGCCTTGGA
AAGGCCACTT TGAACCTCAA TTTTCTCAAC TGTTAAATGG GGTGGTAACT GCTATCTCAT AATAAAGGGG AACGTGAAAG
GAAGGCGTTT GCATAGTGCC TGGTTGTGCA GCCAGGCTGC AGTCAAGACT AGTTCCCACC AACTCGATTT TAAAGCCTTG
CAAGAAGGTG GCTTGTTTGT CCCTTGCAGG TTCCTTTGTC GGGCCAAACT CTAGAATGCC TCCCCCTTTC TTTCTCATTG
AAGAGCAGAC CCAAGTCCGG GTAACAAGGA AGGGTTTCAG GGTCCTGCCC ATAAAAGGTT TTTCCCGGCC GCCCTCAGCA
CCGCCCCGCC CCGACCCCCG CAGCATCTCC AAAGCATGCA GAGAATGTCT CCGGCTGCCC CCGACAGACT GCTCCAACTT
GGTGTCTTTC CCCAAATATG GAGCCTGTGT GGAGTGAGTG GGGCGGCCCG GGTGGTGAG CCAAGCAGAC TTCCATGGGC
AGGGAGGGGC GCCAGCGGAC GGCAGAGGGG TGACATCACT GCCTAGGCGG CCTTTAAACC CCTCACCCAG CCGGCGCCCC
AGCCCGTCTG CCCCAGCCCA GACACCGAAG CTACTCTCCT TCCAGTCCAC AAACGACCAA GCCTTGtcga caagctTGGT
                                                                            start-ATG
ACCGAGCTCG GATCCACTAG TCCAGTGTGG TGGAATTCAT GCTGCTCCCT GTGCCGCTGC TGCTCGGCCT GCTCGGCCTG
                                            ▶Me tLeuLeuPro ValProLeuL euLeuGlyLe uLeuGlyLeu
GCCGCCGCCG AGCCCGTCGT CTACTTCAAG GAGCAGTTTC TGGACGGAGA TGGGTGGACC GAGCGCTGGA TCGAATCCAA
▶AlaAlaAlaG luProValVa lTyrPheLys GluGlnPheL euAspGlyAs pGlyTrpThr GluArgTrpI leGluSerLy
ACACAAGTCC GATTTTGGCA AATTCGTCCT CAGTTCGGGC AAGTTCTACG GCGATCAGGA GAAAGATAAA GGGCTGCAGA
▶sHisLysSer AspPheGlyL ysPheValLe uSerSerGly LysPheTyrG lyAspGlnGl uLysAspLys GlyLeuGlnT
CCAGCCAGGA CGCCCGCTTC TACGCCCTGT CGGCCCGATT CGAGCCGTTC AGCAACAAGG GCCAGCCACT GGTGGTGCAG
▶hrSerGlnAs pAlaArgPhe TyrAlaLeuS erAlaArgPh eGluProPhe SerAsnLysG lyGlnProLe uValValGln
TTCACCGTGA AACACGAGCA GAACATTGAC TGCGGGGGCG GCTACGTGAA GCTGTTTCCG GCCGGCCTGG ACCAGAAGGA
▶PheThrValL ysHisGluGl nAsnIleAsp CysGlyGlyG lyTyrValLy sLeuPhePro AlaGlyLeuA spGlnLysAs
CATGCACGGG GACTCTGAGT ACAACATCAT GTTTGGTCCT GACATCTGTG GCCCCGGCAC CAAGAAGGTT CACGTCATCT
▶pMetHisGly AspSerGluT yrAsnIleMe tPheGlyPro AspIleCysG lyProGlyTh rLysLysVal HisValIleP
TCAACTACAA GGGCAAGAAC GTGCTGATCA ACAAGGACAT CCGTTGCAAG GACGACGAGT TCACACACCT GTACACGCTG
▶heAsnTyrLy sGlyLysAsn ValLeuIleA snLysAspIl eArgCysLys AspAspGluP heThrHisLe uTyrThrLeu
ATCGTGCGGC CGGACAACAC GTATGAGGTG AAGATTGACA ACAGCCAGGT GGAGTCGGGC TCCCTGGAGG ATGACTGGGA
▶IleValArgP roAspAsnTh rTyrGluVal LysIleAspA snSerGlnVa lGluSerGly SerLeuGluA spAspTrpAs
CTTCCTACCC CCCAAGAAGA TAAAGGACCC AGATGCCTCG AAGCCTGAAG ACTGGGACGA GCGGGCCAAG ATCGACGACC
▶pPheLeuPro ProLysLysI leLysAspPr oAspAlaSer LysProGluA spTrpAspGl uArgAlaLys IleAspAspP
CCACGGACTC CAAGCCCGAG GACTGGGACA AGCCCGAGCA CATCCCCGAC CCGGACGCGA AGAAGCCCGA AGACTGGGAC
▶roThrAspSe rLysProGlu AspTrpAspL ysProGluHi sIleProAsp ProAspAlaL ysLysProGl uAspTrpAsp
GAAGAAATGG ACGGAGAGTG GGAGCCGCCG GTGATTCAGA ACCCCGAGTA CAAGGGTGAG TGGAAGCCGC GGCAGATCGA
▶GluGluMetA spGlyGluTr pGluProPro ValIleGlnA snProGluTy rLysGlyGlu TrpLysProA rgGlnIleAs
CAACCCCGAT TACAAAGGCA CCTGGATCCA CCCCGAAATC GACAACCCCG AGTACTGCGC CGACGCTAAC ATCTATGCCT
▶pAsnProAsp TyrLysGlyT hrTrpIleHi sProGluIle AspAsnProG luTyrSerPr oAspAlaAsn IleTyrAlaT
ACGACAGCTT TGCCGTGCTG GGCTTGGACC TCTGGCAGGT CAAGTCGGGC ACCATCTTCG ACAACTTCCT CATCACCAAC
▶yrAspSerPh eAlaValLeu GlyLeuAspL euTrpGlnVa lLysSerGly ThrIlePheA spAsnPheLe uIleThrAsn
GATGAGGCGT ACGCAGAGGA GTTTGGCAAC GAGACGTGGG GCGTCACCAA GACGGCCGAG AAGCAGATGA AAGACAAGCA
▶AspGluAlaT yrAlaGluGl uPheGlyAsn GluThrTrpG lyValThrLy sThrAlaGlu LysGlnMetL ysAspLysGl
GGACGAGGAG CAGCGGCTGA AGGAGGAGGA GGAGGAGAAG AAGCGGAAGG AGGAGGAGGA GGCCGAGGAG GACGAGGAGG
▶nAspGluGlu GlnArgLeuL ysGluGluGl uGluGluLys LysArgLysG luGluGluGl uAlaGluGlu AspGluGluA
ACAAGGACGA CAAGGAGGAC GAGGATGAGG ACGAGGAGGA CAAGGACGAG GAGGAGGAGG AGGCGGCCGC CGGCCTCGAG
▶spLysAspAs pLysGluAsp GluAspGluA spGluGluAs pLysAspGlu GluGluGluG luAlaAlaAl aGlyLeuGlu
  HA Tag (green)
TACCCATATG ATGTTCCTGA CTATGCTAGA CAGGCCAAGG ACGAGCTGTA G
▶TyrProTyrA spValProAs pTyrAlaArg GlnAlaLysA spGluLeu·· ·
```

TRANSGENIC MOUSE OVER-EXPRESSING CALRETICULIN (CRT) IN VASCULAR SMOOTH MUSCLE CELLS

PRIOR APPLICATION INFORMATION

This application claims priority on U.S. Ser. No. 60/455,399, filed Mar. 18, 2003.

FIELD OF THE INVENTION

The present invention relates generally to the field of animal models for human diseases. More specifically, it relates to a transgenic mouse usable as an animal model for hemangioendothelioma.

BACKGROUND OF THE INVENTION

Transgenic mice technology involves the introduction of new or altered genetic material into the mouse germ line. This results in lineages that carry the new integrated genetic material.

Endoplasmic reticulum (ER) plays an important role in many functions of the cell. ER is not only the protein folding and processing machinery of the cell but it plays an important role in $Ca^{2+}$ storage and regulation of intracellular $Ca^{2+}$ homeostasis (Pozzan et al., 1994). It is also important in gene regulation (unfolded protein response) (Tirasophon et al., 1998; Welihinda et al., 1997). There are a number of ER resident proteins (including CRT) which are essential for the proper implementation of these functions.

Studies on tumor angiogenesis have resulted in a significant progress in our understanding of the genetic and molecular mechanisms that control the development of the vascular system. The embryonic origin of the vascular system is best understood with respect to endothelial cells (Cleaver and Krieg, 1999). These cells are the defining cell types of the vascular system. During embryogenesis, these cells differentiate (from angioblast origin), migrate, and assemble into the vascular network. Subsequently pericytes are recruited to the periphery of the endothelium and differentiate into vascular smooth muscle cells (Manasek, 1971).

The formation of the vascular system is achieved by the coordination of two processes, namely vasculogenesis and angiogenesis (Risau and Lemmon, 1988), (Pardanaud et al., 1989). Vasculogenesis is the first step in vascular development leading to layout of the initial primitive vascular network, the capillary plexus (Risau and Flamme, 1995). Angiogenesis is a later process, which involves the sprouting, branching and differential growth of blood vessels to form the mature vessel (Risau and Flamme, 1995). There are two types of angiogenesis: sprouting angiogenesis, involving true sprouting of capillaries from preexisting blood vessels, and non-sprouting angiogenesis (or intussusception) which involves the splitting of preexisting vessels (Folkman and Klagsbrun, 1987; Klagsbrun and D'Amore, 1991; Patan et al., 1996). Vascularization of tissues like the yolk sac, embryonic brain, kidney, thymus, limb bud and intersomitic vessels are formed by sprouting angiogenesis (Ekblom et al., 1982; Le Lievre and Le Douarin, 1975; Bar, 1980; Joterau and Le Douarin, 1978; Stewart and Wiley, 1981; Coffin and Poole, 1988). However, in the developing lung, myocardium, chorioallantoic membrane, endothelial wound healing and the development of coronary arteries, vascularization occurs by non-sprouting, or intussusception angiogenesis (Flamme and Risau, 1992; Burri and Tarek, 1990; van Groningen et al., 1991; Patan et al., 1993; Patan et al., 1996; Reidy and Schwartz, 1981; Bogers et al., 1989).

A large number of molecules can affect angiogenesis and vasculogenesis, including a number of growth factors, their receptors, and components of the extracellular matrix (ECM) (reviewed in Cleaver and Krieg, 1999). The receptor tyrosine kinases expressed on the surface of endothelial cells also play important roles in initiating the program of endothelial cell growth during development and subsequent vascularization during wound healing and tumorigenesis. VEGF and its receptor Flk-1 are thought to be responsible for both primary vessel formations during vasculogenesis and angiogenic invasion of the developing organs (Flamme et al., 1995; Cleaver et al., 1997; Cleaver and Krieg, 1999). Both Flk-1 and Flt-1 (placental growth factor receptor) are expressed exclusively in the endothelial cells (Flamme et al., 1995; Peters et al., 1993). Tie-2 is another receptor tyrosine kinase which is highly expressed in the endothelial cells during embryogenesis and adult life (Davis et al., 1996; Suri et al., 1996). This receptor and its ligands, angiopoietin-1 and 2, are involved in angiogenesis and later vascular remodeling (Dumont et al., 1995; Sato et al., 1995). Targeted disruption of the Tie-2 gene in mice resulted in embryonic lethality due to defects in the integrity of the endothelium, and consequently defects in cardiac and vascular development (Dumont et al., 1992; Dumont et al., 1994; Dumont et al., 1995). These observations demonstrate that the Tie-2 signaling pathway plays a critical role in the differentiation, proliferation, and survival of endothelial cells as well as heart development in the mouse embryo (Dumont et al., 1994; Sato et al., 1995). Because gene targeted deletion of CRT results in similar cardiovascular defects in the embryos (Mesaeli et al., 1999), one may hypothesize that CRT plays a role in the growth factor signaling pathway. Indeed, an inverse relationship between expression of CRT and total cellular tyrosine phosphorylation level has been reported in cultured cells (Fadel et al., 1999) suggesting that the protein may affect tyrosine phosphorylation-dependent signaling.

The ECM and cell adhesion proteins can also regulate the process of vasculogenesis and angiogenesis by modulating growth, differentiation and migration of the endothelial cells (Risau and Lemmon, 1988; Ausprunk et al., 1991). For example, fibronectin is essential for the assembly of the vessel (Risau and Lemmon, 1988; Hynes, 1990), while collagen and laminin become important in later stages of vessel development (Hynes, 1990). Blocking of $\alpha_5\beta_1$ integrin function results in major defects in early vasculogenesis (Drake et al., 1992; Yang et al., 1993). Blocking the $\beta_3$ family of integrins results in defects in angiogenesis and vascular cell survival (Brooks et al., 1994a; Brooks et al., 1994b). CRT may influence vessel formation through regulating the expression and function of cell adhesion proteins. For example differential expression of CRT affects integrin function (Leung-Hagesteijn et al., 1994; Coppolino et al., 1997). In addition, overexpression of CRT results in up-regulation of vinculin and N-cadherin (Fadel et al., 1999; Opas et al., 1996). It is still presently unclear if CRT alters angiogenesis through an effect on ECM or cell adhesion proteins or both.

SUMMARY OF THE INVENTION

According to a first aspect of the invention, there is provided a transgenic mouse whose genome comprises a transgene comprising a transcriptional control region operably linked to a cDNA encoding calreticulin (CRT) wherein said control region comprises a promoter wherein expression of calreticulin in the vascular smooth muscle cells (VSMC) results in hemangioma formation.

According to a second aspect of the invention, there is provided a transgene comprising a transcriptional control region operably linked to a cDNA encoding calreticulin wherein said control region comprises a SM22α promoter.

According to a third aspect of the invention, there is provided a method for producing a transgenic mouse whose genome comprises CRT comprising:

introducing into a fertilized mouse egg a transgene comprising a transcriptional control region operably linked to a cDNA encoding CRT wherein said control region comprises a promoter;

transplanting the injected egg in a foster parent female mouse; and selecting a mouse derived from an injected egg whose genome comprises CRT.

According to a fourth aspect of the invention, there is provided a method for screening compounds that inhibit vascular tumor formation in a transgenic mouse comprising providing a transgenic mouse whose genome comprises a transgene comprising a transcriptional control region operably linked to a cDNA encoding calreticulin (CRT);

allowing CRT to be expressed in VSMC of said transgenic mouse administering a compound to said mouse; and determining whether said compound reduces hemangioma formation.

According to a fifth aspect of the invention, there is provided a method of testing the therapeutic activity of a pharmacological agent on hemangioenothelioma comprising administering an effective amount of said pharmacological agent to the mouse described above and evaluating said agent's effect on hemangioma formation of said mouse. In some embodiments, the hemangioenothelioma may be Kaposiform hemangioenothelioma.

According to a sixth aspect of the invention, there is provided a method of inhibiting hemangioma formation comprising administering an effective amount of a matrix metalloproteinase inhibitor to a patient in need of such treatment. Chemical inhibitors of matrix metalloproteinase include MMP-2/MMP-9 inhibitor I (2R)-2-[(4-Biphenylylsulfonyl)amino]-3-phenylpropionic Acid, $IC_{50}=240–350$ nM), MMP-2/MMP-9 inhibitor II ($IC_{50}=17–30$ nM), MMP-2/MMP-9 inhibitor III ($IC_{50}=10$ µM), and Chlorhexidine (Dihydrochloride). Alternatively, adeno-associated virus can be used to deliver the cDNA of TIMP-1 (Tissue inhibitor of matrix metalloproteinase) or TIMP-2 intravenously.

Patients diagnosed with hemangioendothelioma due to the presence of skin lesions (red/blue nodule on the skin at early cases) or deep soft tissue tumor can be treated with these inhibitors and the effect on the tumor size and progress could be studied over time.

According to a seventh aspect of the invention, there is provided a method of inhibiting hemangioma comprising administering to an individual in need of such treatment an effective amount of virally-administered small interference RNA (SiRNA) corresponding to a portion of CRT mRNA, wherein expression of the SiRNA decreases the level of CRT. The siRNA will be generated corresponding to the nucleotide 1917–1937 of SEQ ID NO. 1, the DNA sequence in FIG. 16 (sequences of sense 5'-GCU GAU CGU GCG GCC GGA CAA dTT 3', and anti-sense 5'-UUG UCC GGC CGC ACG AUC AGC dTT 3'). This siRNA has been shown to significantly diminish the expression of CRT (Troussard et. al., 2003).

BRIEF DESCRIPTION OF THE DRAWINGS

FIG. 16—Nucleotide and amino acid sequence of SM22α-CRT (SEQ ID No. 1).

FIG. 17—Nucleotide and amino acid sequence of SM22α-CRT-HA (SEQ ID No. 12).

DESCRIPTION OF THE PREFERRED EMBODIMENTS

Figure 1:
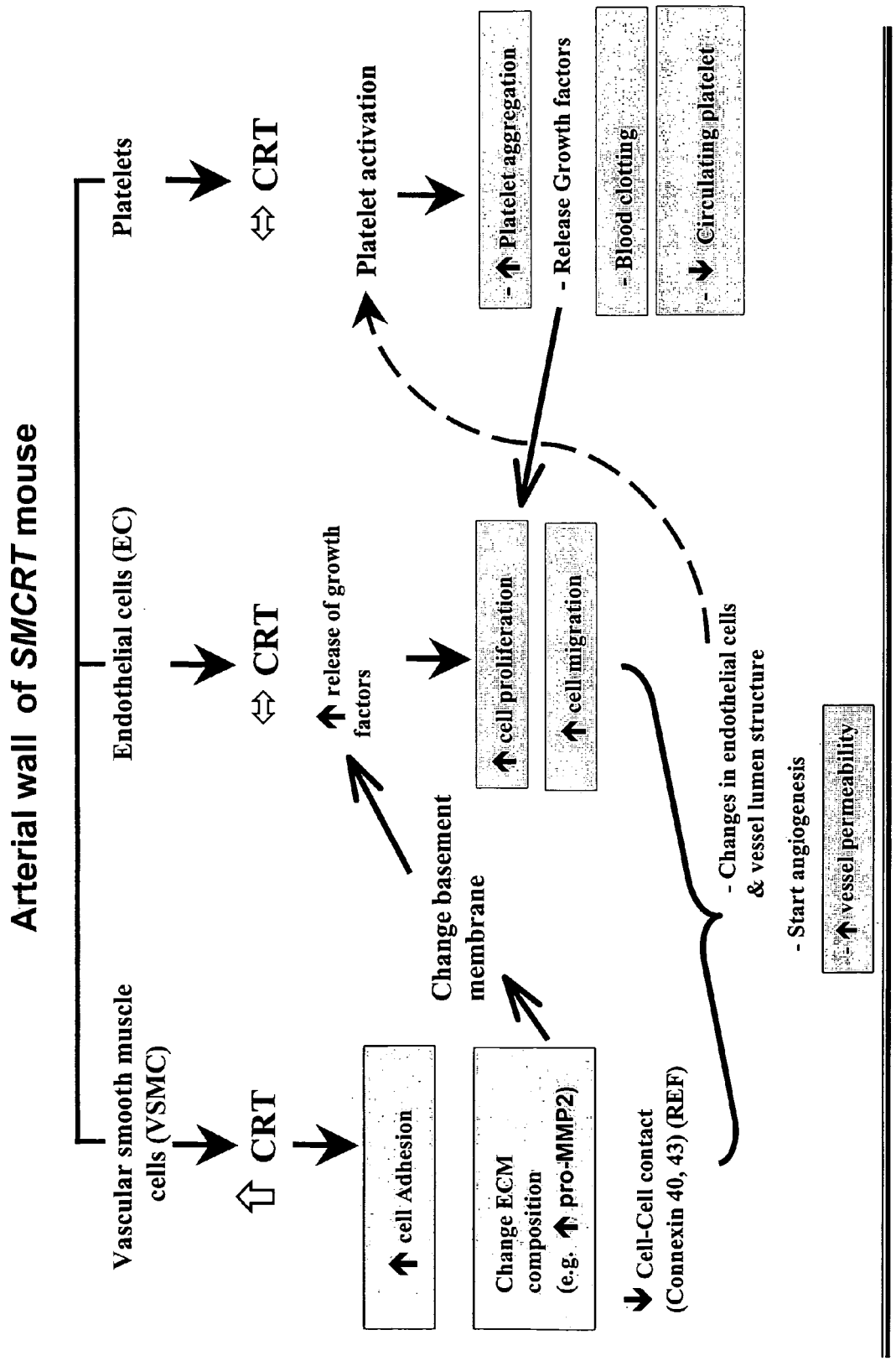
FIG. 1—Schematic diagram showing the possible mechanism for the development of hemangioendothelioma in the SMCRT mice. Yellow boxes are items which will be tested.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, "calreticulin" or CRT, depending on the context, refers to a peptide encoding CRT as shown in FIG. 16 or 17, a cDNA encoding CRT as shown in FIG. 16 or 17, a cDNA molecule deduced from said peptide sequence, or a bioactive fragment or mutant or variant, either inter-species or intra-species, form thereof. As will be appreciated by one of skill in the art, a variant may be CRT from a different species which has at least 60% homology, or at least 70% homology or at least 80% homology to CRT amino acid sequence shown in FIG. 16 (SEQ ID No. 23) or is a peptide known or believed to be related to or functionally homologous to CRT or a bioactive fragment thereof. As used herein, "bioactive" with regard CRT indicates that the fragment or mutant form of CRT retains substantially normal or biological CRT activity.

As used herein, "Kasbach-Merritt Syndrome" refers to a syndrome characterized by very extensive and progressively enlarging vascular malformation that may involve large portions of the patient's extremities. In this syndrome, bleeding is secondary to disseminated intravascular coagulation triggered by stagnant blood flow through the tortuous vessels.

As used herein, "hemangiomas" refer to tumor-like clusters of proliferating capillaries or abnormally dense collections of dilated small blood vessels that occur in skin or internal organs. Hemangiomas may be for example surface hemangiomas or cavernous hemangiomas. Kaposiform hemangioendothelioma (KHE) refers to a very aggressive form of hemangioma, often accompanied by platelet trapping and thrombocytopenia.

As used herein, "hemangioendothelioma" refers to proliferative and neoplastic vascular lesions, including hemangiomas.

Described herein is the preparation of a transgenic mouse arranged to express calreticulin (CRT) in vascular smooth muscle cells. This results in a mouse having symptoms similar to Kasbach-Merritt Syndrome. By expressing CRT in vascular smooth muscle cells, transgenic mice usable as animal models for hemangioendothelioma can be prepared. That is, the transgenic mouse can be used to study many aspects of hemangioendothelioma, including the molecular mechanism of tumor formation, cell type involvement and efficacy of potential treatments.

The CRT is stably integrated within the SMCRT mouse genome, meaning that any offspring mice will express the same traits as their parents. Thus, the obtained transgenic mice can be used to conduct experiments with extremely high reproducibility.

In one embodiment of the invention, there is provided a transgenic mouse whose genome comprises a transgene comprising a transcriptional control region operably linked to a cDNA encoding calreticulin (CRT) wherein said control region comprises a promoter wherein expression of calreticulin in the vascular wall results in hemangioma formation. In some embodiments, the promoter is a vascular smooth muscle-specific promoter, for example, SM22α promoter. As will be appreciated by one of skill in the art, the cDNA encoding CRT may be as shown in FIG. 16 or may be deduced from the amino acid sequence of CRT as shown in FIG. 16. In other embodiments, the cDNA sequence within the transgene may include sequence variations, for example, mutations and deletions, which do not significantly affect or alter the normal, biological function of CRT.

In another embodiment of the invention, there is provided a transgene comprising a transcriptional control region operably linked to a cDNA encoding calreticulin wherein said control region comprises a SM22α promoter, as shown in FIG. 16. In another embodiment, the transgene includes a tag for distinguishing between transgenic CRT and endogenous CRT, as shown in FIG. 17 and as discussed below. In the embodiment shown in FIG. 17, the tag is HA although other suitable tags known in the art may also be used.

In another aspect of the invention, there is provided a method for producing a transgenic mouse whose genome comprises CRT comprising: introducing into a fertilized mouse egg a transgene comprising a transcriptional control region operably linked to a cDNA encoding CRT wherein said control region comprises a promoter; transplanting the injected egg in a foster parent female mouse; and selecting a mouse derived from an injected egg whose genome comprises CRT. As will be appreciated by one of skill in the art, the transgene may be introduced into the mouse egg by any of a number of suitable methods known in the art.

In another embodiment of the invention, there is provided a method for screening compounds that inhibit vascular tumor formation in a transgenic mouse comprising providing a transgenic mouse whose genome comprises a transgene comprising a transcriptional control region operably linked to a cDNA encoding calreticulin (CRT); allowing CRT to be expressed in said transgenic mouse administering a compound to said mouse; and determining whether said compound reduces hemangioma formation. In these embodiments, the hemangioma in the mouse treated with the compound may be compared to hemangioma in an untreated control and the difference between the treated mouse and untreated control used to determine efficacy of the compound. Examples of human vascular tumors include but are by no means limited to cavernous hemaginoma, Kaposi's sarcoma or those characterizing Kasabach-Merritt syndrome.

In one embodiment of the invention, there is provided a method of inhibiting hemangioma formation comprising administering an effective amount of a matrix metalloproteinase inhibitor to a patient in need of such treatment. As discussed below, transgenic mice expressing CRT show increased matrix metalloproteinase-2 (MMP-2) and matrix metalloproteinase-9 (MMP-9) activity compared to wild type mice. Thus, inhibiting MMP activity will accomplish at least one of the following: reduce frequency of hemangioma formation, reduce size and/or severity of hemangioma, inhibit or reduce hemangioma formation, and treat or ameliorate at least one symptom associated with hemangioma formation.

Chemical inhibitors of matrix metalloproteinase include but are by no means limited to MMP-2/MMP-9 inhibitor I (2R)-2-[(4-Biphenylylsulfonyl)amino]-3-phenylpropionic Acid, $IC_{50}$=240–350 nM), MMP-2/MMP-9 inhibitor 11 ($IC_{50}$=17–30 nM), MMP-2/MMP-9 inhibitor III ($IC_{50}$=10 μM), and Chlorhexidine (Dihydrochloride). Alternatively, adeno-associated virus can be used to deliver the cDNA of TIMP-1 (Tissue inhibitor of matrix metalloproteinase) or TIMP-2 intravenously. As will be appreciated by one of skill in the art, the concentrations provided above are for illustrative purposes only and the exact dosage that comprises an "effective amount" of an MMP inhibitor may vary according to the weight, health, age and/or overall condition of a patient, but will be the dosage that is sufficient to complete the intended purpose, that is, inhibit hemangioma formation as discussed above.

Patients diagnosed with hemangioendothelioma due to the presence of skin lesions (red/blue nodule on the skin at early cases) or deep soft tissue tumor can be treated with these inhibitors and the effect on the tumor size and progress could be studied over time.

In another embodiment of the invention, there is provided a method of inhibiting hemangioma comprising administering to an individual in need of such treatment an effective amount of virally-administered small interference RNA (siRNA) corresponding to a portion of CRT mRNA, wherein expression of the siRNA decreases the level of CRT. Efficient and stable expression of siRNA can be achieved by gene delivery using means known in the art, for example, using lentiviral plasmids which are available commercially (Invitrogen).

In another embodiment of the invention, there is provided a method of testing the therapeutic activity of a pharmacological agent on hemangioenothelioma comprising administering an effective amount of said pharmacological agent to the above-described transgenic mouse and evaluating said agent's effect on hemangioma formation of said mouse. As will be appreciated by one of skill in the art, the evaluation may comprise detecting for example a decrease in hemangioma size or formation compared to an untreated or mock-treated control. It is important to note that in the process, the control does not necessarily need to be repeated with each trial. It is of note that the pharmacological agent may be for example a peptide or peptide fragment, a small molecule, a chemical compound, a nucleic acid or the like.

Several lines of evidence suggest a role for calreticulin (CRT) in the process of angiogenesis by affecting cell adhesion, migration and proliferation. CRT is expressed in different cells of the vascular wall (Mesaeli and Michalak, 1995; Mesaeli et al., 1999; Milner et al., 1991; Tharin et al., 1992). CRT gene is also activated in the vascular bed early in mouse development (Mesaeli et al., 1999). Exogenously added CRT to the vascular cells or vessel lumen alters different aspects of vascular function. For example, in adult rats, exogenously added CRT acts as a vascular regulatory protein by reducing intimal hyperplasia (restenosis) after arterial injury (Dai et al., 1997). It also selectively inhibits endothelial cell proliferation when added to the endothelial culture media (Pike et al., 1999). Although these data postulate a role for CRT in the angiogenic process, direct evidence is not available. To investigate the role of CRT in vascular cell function, we generated a transgenic mouse overexpressing CRT in the vascular smooth muscle cells (hereafter will be referred to as SMCRT) using a truncated form of the SM22α promoter. These mice die at an adult stage. The overall symptoms of these mice are similar to the symptoms of the human patients with Kasabach-Merritt Syndrome. The main abnormality in the SMCRT mice is the development of "Giant hemangioma" associated with the outflow tract of the heart and the presence of hemangioma on the skin. Our results also show increased branching and vascularization of the coronary arteries accompanied by dilation of the heart. Other phenotypes of these mice are lung and kidney congestion (resembling congestive heart failure). In mice at an end stage of the disease, we have observed blood clots in the adipose tissue surrounding the kidneys and the presence of blood clots in the kidney capsule. These defects indicate vascular wall remodeling accompanied by increased microvascular permeability leading to tumor formation in these mice.

CRT is a ubiquitous eukaryotic protein which shares a high degree of identity among all the different species (Michalak, 1996). CRT is the product of translation of a single mRNA (Michalak, 1996), resulting in a 46 kDa protein which is localized to the lumen of ER and nuclear envelope (Michalak et al., 1992; Milner et al., 1992; Michalak, 1996). Several unique functions have been postulated for CRT (reviewed in Michalak et al., 1999), including chaperone activity (Nauseef et al., 1995; Nigam et al., 1994; Hebert et al., 1997), regulation of cell adhesion (Coppolino et al., 1995; Coppolino et al., 1997; Opas et al., 1996), modulation of steroid mediated gene expression (Burns et al., 1994; Dedhar et al., 1994; Michalak et al., 1996; Wheeler et al., 1995; Winrow et al., 1995), and regulation of $Ca^{2+}$ homeostasis (Bastianutto et al., 1995; Camacho and Lechleiter, 1995; Coppolino et al., 1997; Liu et al., 1994; Mery et al., 1996).

Chaperone function of CRT—CRT is a lectin-like chaperone (Hammond and Helenius, 1995; Peterson et al., 1995; Spiro et al., 1996), involved in the "quality control" process during the synthesis and folding of a variety of proteins including cell surface receptors, integrins and transporters (Helenius et al., 1997). CRT binds the terminal glucose of the oligosaccharide moiety of the unfolded protein. During the folding process, the newly synthesized protein can go through many cycles of binding and release from the lectin-like chaperone by removal and addition of this terminal glucose (involving glucosidase I and II, and UDP-glucose transferase, respectively). This results in the proper processing of the protein. If the protein is misfolded, it will accumulate in the cell triggering an "unfolded protein response" and starting protein degradation. In the CRT null mouse embryonic fibroblast cells, we have observed an increase in the expression of a number of ER chaperones; however the function of these chaperones seems to be compromised (Mesaeli et al., 2000). Indeed, the unfolded protein response in these cells is stimulated as evident by a significant (100%) increase in the expression of BiP (Grp78) (Mesaeli et al., 2000). CRT has been shown to be bind to glycosylated laminin in the ER (McDonnell et al., 1996) perhaps affecting its folding. Overexpression of CRT has been shown to increase the level of pro-MMP2 protein (Ito et al., 2001). Other proteins which have been shown to be malformed in absence of CRT includes: bradykinin receptor (Nakamura et al., 2001b), MHC class I protein (Gao et al., 2002), $IP_3$ receptor (all three isoforms) (Paziuk and Mesaeli, 2002), and connexin 43 protein which fails to localize to the cell-cell junction in the heart (Ahmadi et al., 2002). Interestingly, overexpression of CRT in the hearts of transgenic mice resulted in a decrease in the expression of connexin 40 and 43 (Nakamura et al., 2001a).

CRT and cell adhesion—The first evidence for the possible role of CRT in cell adhesion came from in vitro studies designed to identify the cellular proteins which bind to KxFF(k/R)R peptide (Rojiani et al., 1991), a consensus sequence in the C-terminal tail of the α-subunit of integrin. However, recent reports indicate that CRT may influence cell adhesion indirectly via modulation of gene expression of adhesion related molecules (Fadel et al., 1999; Opas et al., 1996), or by changes in the integrin-dependent $Ca^{2+}$ signaling (Coppolino et al., 1997). Overexpression of CRT results in up-regulation of vinculin and N-cadherin (Fadel et al., 1999; Opas et al., 1996), resulting in an increase in cell-substratum attachment. Down regulation of CRT results in an opposite effect (Leung-Hagesteijn et al., 1994; Opas et al., 1996). Protein tyrosine phosphorylation/dephosphorylation comprises one of the major mechanisms in regulating cell adhesion (Burridge and Chrzanowska-Wodnicka, 1996), (Cox and Huttenlocher, 1998; Daniel and Reynolds, 1997). Previously, we have reported a significant decrease in the level of tyrosine phosphorylation in fibroblast cells overexpressing CRT (Fadel et al., 1999) which coincided with changes in cell adhesiveness.

CRT and intracellular $Ca^{2+}$—CRT was initially discovered as a $Ca^{2+}$ binding protein in the lumen of ER (Ostwald et al., 1974), (Michalak et al., 1980). The protein has two $Ca^{2+}$ binding sites: a high affinity, low capacity site and a low capacity, high affinity site (Ostwald et al., 1974), (Baksh and Michalak, 1991). Overexpression of CRT results in an increased level of intracellular $Ca^{2+}$, however, it does not affect the cytosolic free $Ca^{2+}$ concentration (Bastianutto et al., 1995), (Mery et al., 1996), (Michalak et al., 1996; Opas et al., 1996). Knockout of the CRT gene did not result in a change in the $Ca^{2+}$ storage capacity of the ER in ES cells and in mouse embryonic fibroblast cells (Coppolino et al., 1997; Mesaeli et al., 1999). However, CRT deficient mouse embryonic fibroblast cells have decreased agonist-mediated $IP_3$-dependent $Ca^{2+}$ release from ER (Mesaeli et al., 1999). CRT deficient ES cells also showed a defect in integrin mediated $Ca^{2+}$ signaling (Coppolino et al., 1997). These results suggest a change in the expression of CRT can alter cellular $Ca^{2+}$ homeostasis which in turn can affect many cell signaling pathways including cell adhesion (via integrin).

Figure 2:
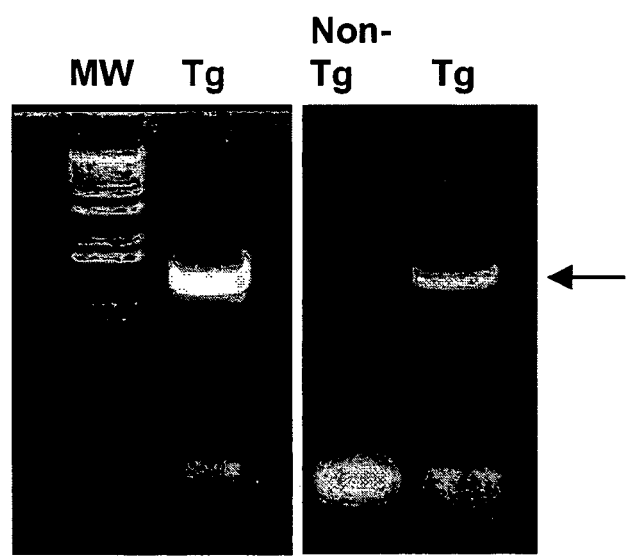
FIG. 2. PCR and western blot showing the genotype and the expression of HA-CRT in the tissue from SMCRT transgenic (Tg) mice and non transgenic litter-mate (Non-Tg). A) Genomic DNA isolated from tail biopsy was used as a template for PCR with primers for HA and CRT cDNA. B) A piece of tail biopsy (containing tail vessels) or descending aorta was homogenized in RIPA buffer, containing protease inhibitors, and centrifuged to remove cellular debris. 20 µg of protein was then separated on 10% SDS acrylamide gel and transferred to nitrocellulose membrane. Membranes were probed with a polyclonal anti-HA antibody.
Figure 2:
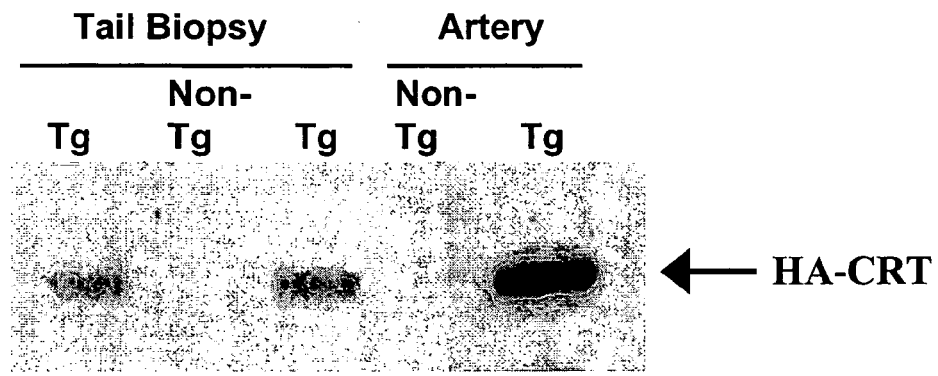
Figure 3:
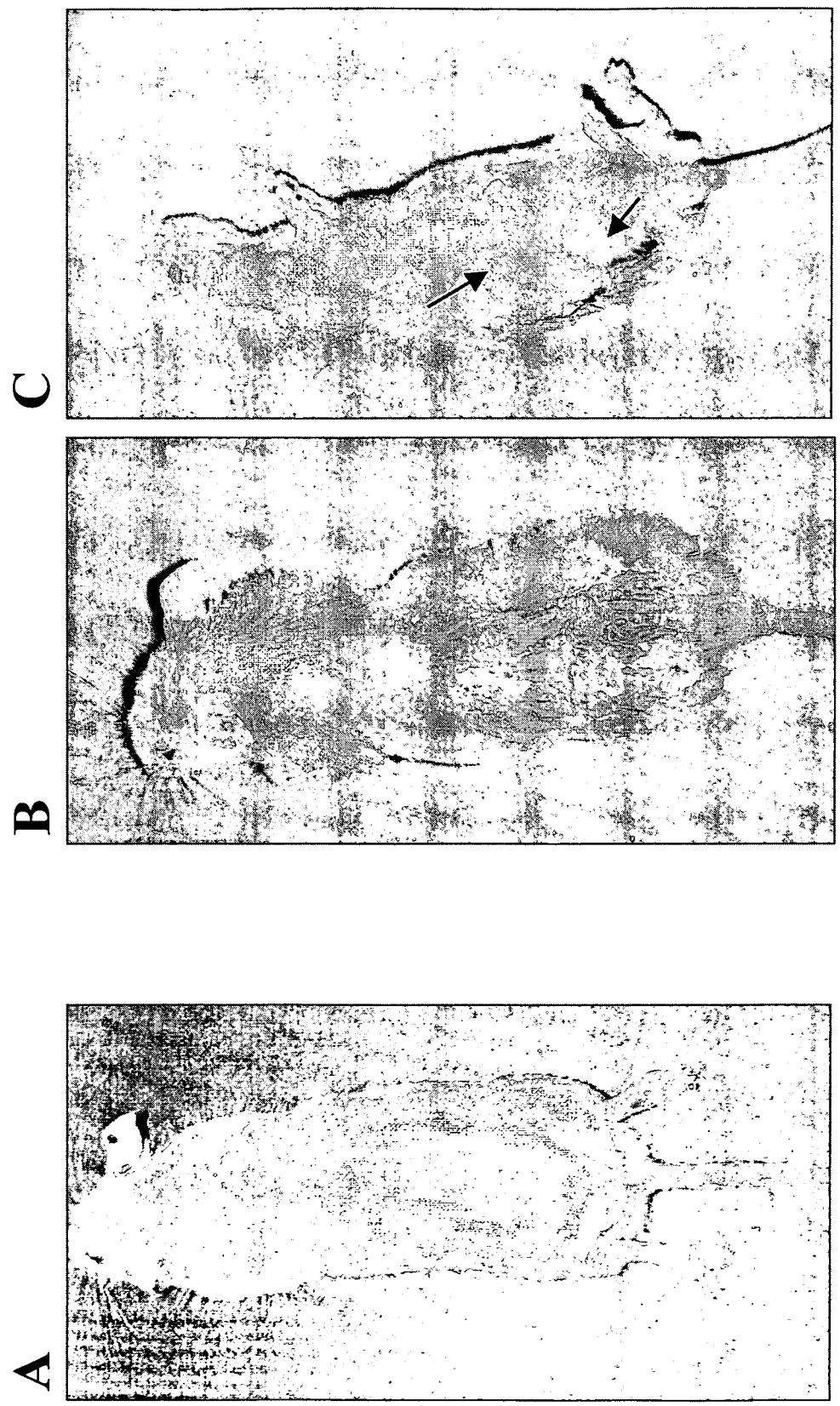
FIG. 3. Skin hemangioma in two lines of the SMCRT transgenic mice. The mouse in A showing the presence of smaller skin lesion, it also had a hemangioendothelioma in the chest originating from the aorta. B and C are images of the same mouse showing a larger hemangioma on the skin. This mouse was anesthetized and shaved to be able to see the size of the tumor. Arrows in C shows some of the skin vasculature surrounding the tumor. This mouse also had a large tumor originating from the heart which has also invaded the lungs.
Figure 4:
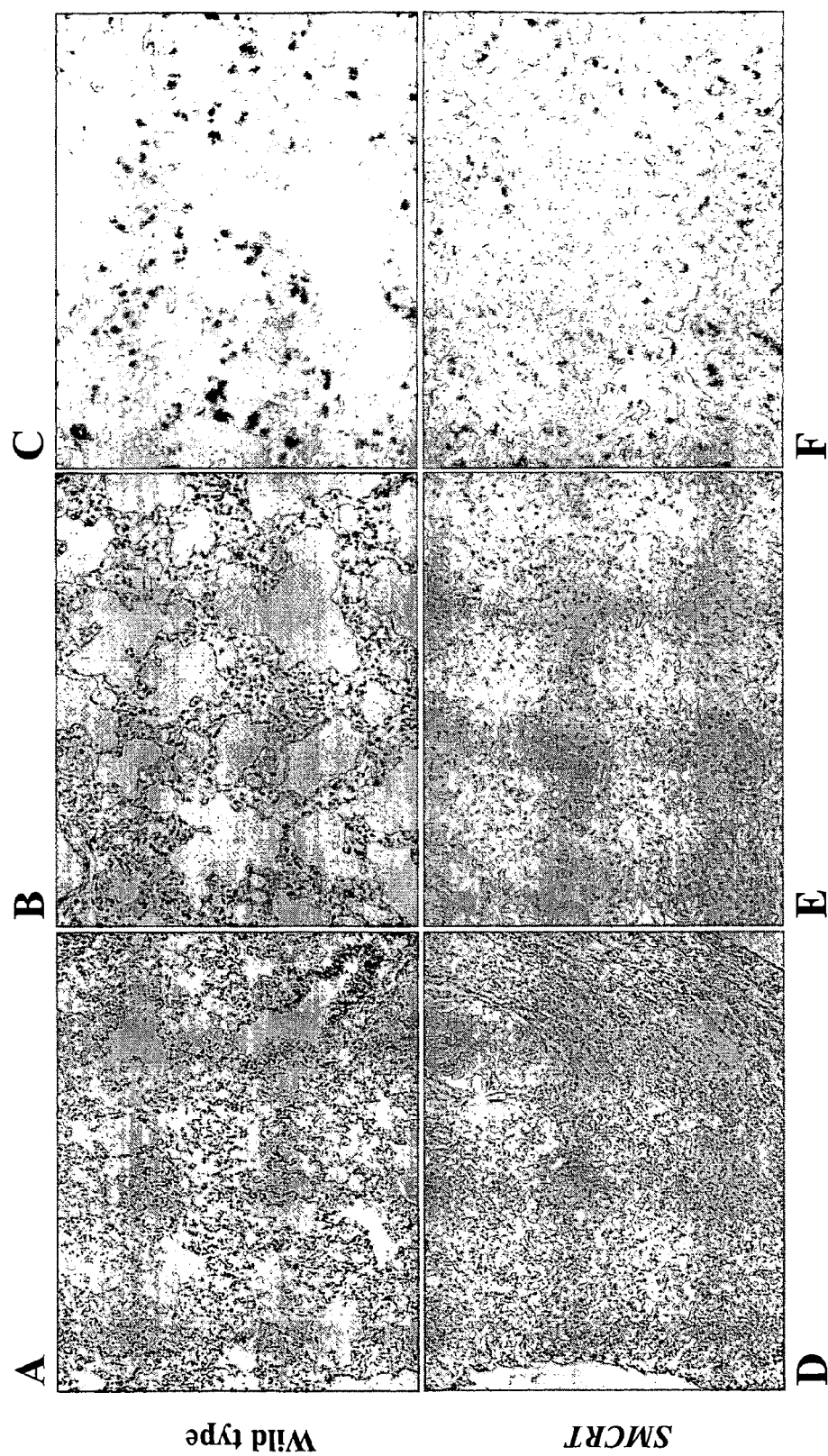
FIG. 4. Histological structure of the Lungs from the wild type (A, B, C) and SMCRT (D, E, F) age matched mice. The SMCRT lung is congested and there is less alveolar spaces. Images are taken at three different magnifications (A, D) at 10×, (B, E) are at 20× and (C, F) are at 40×.
Figure 5:
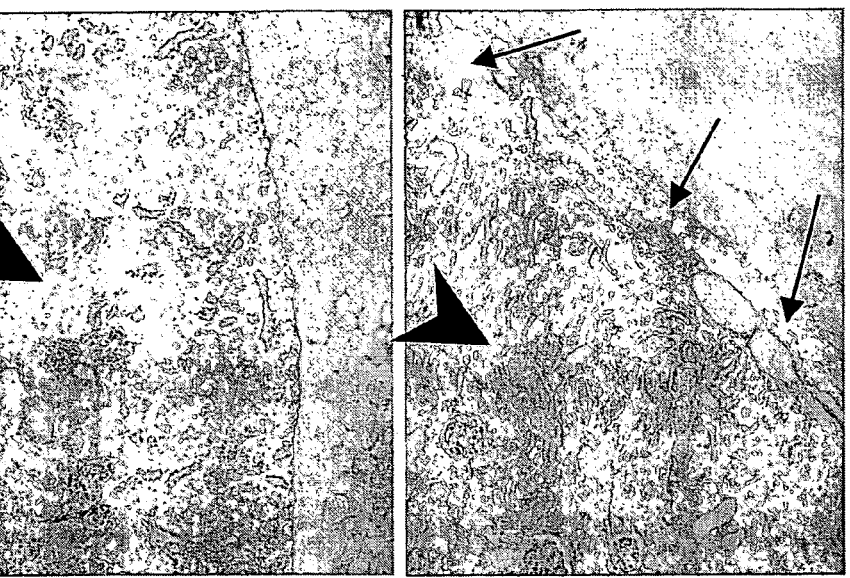
FIG. 5. Picture of the kidney (A) from a SMCRT mouse showing hemorrhage from the renal vessels and sub-capsule bleeding (blood clot, arrows) in the kidney. (B, C) show histology of the kidney from an adult wild type and SMCRT mice kidneys, zooming on the kidney cortex and capsule. Arrows in (C) shows the accumulation of blood in the kidney capsule of the SMCRT kidney. Arrowheads in B,C show the normal tissue of the kidney cortex.
Figure 5:
Figure 6:
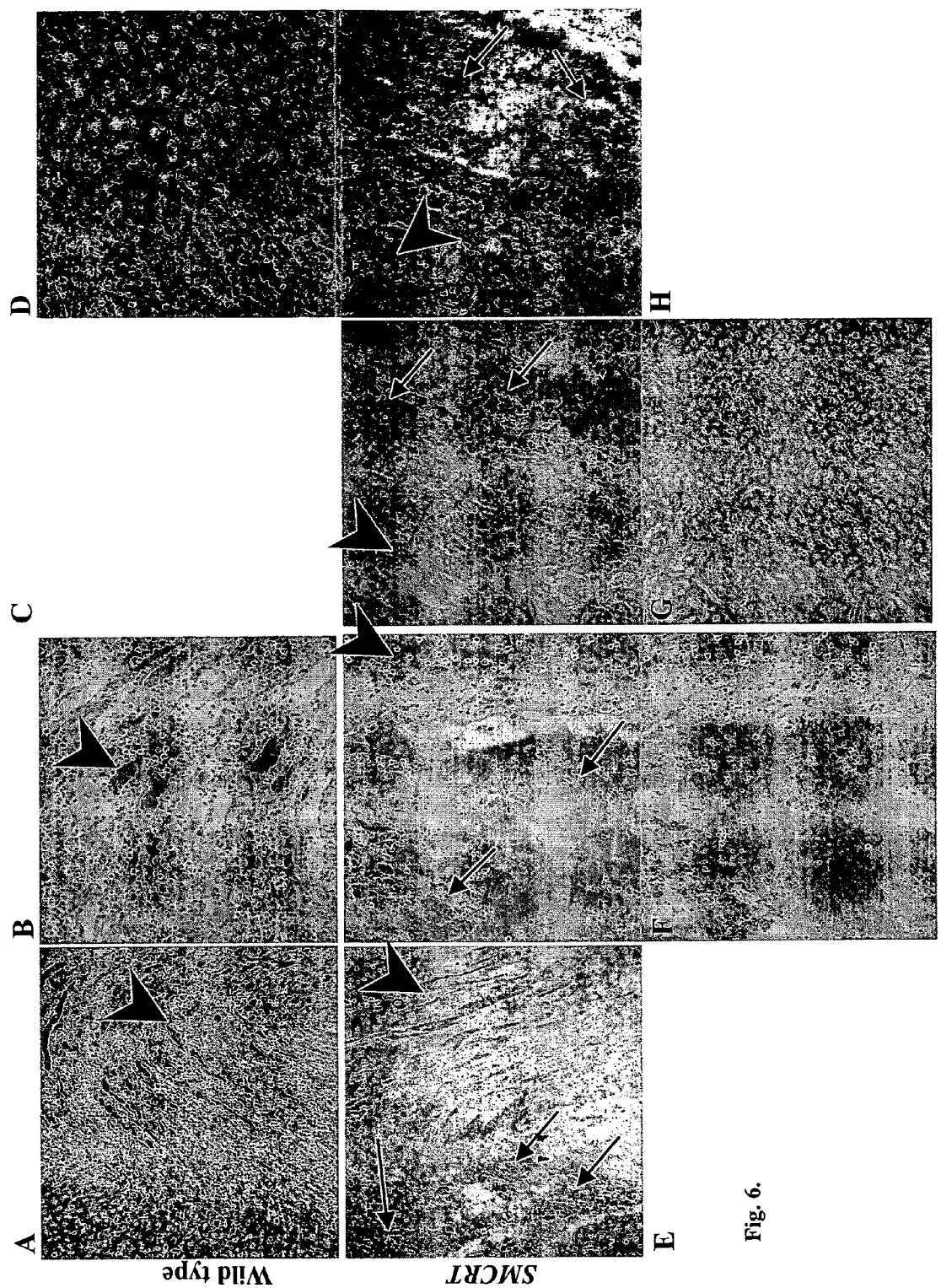
FIG. 6. Histological structure of the kidney from wild type (A, B, C, D) and a SMCRT mouse (E, F, G, H). (A, B) and (E, F) are images from the medulla of the kidney, arrow heads pointing to the kidney tubules in the inner medulla while arrows in (E, F) points to the blood accumulation in the medulla and necrotic region. (C, D) and (G, H) are images from the kidney outer medulla. Arrows in (G, H) show the necrotic area and bleeding in this region of the SMCRT, while the arrow heads show the normal tissue.
Figure 7:
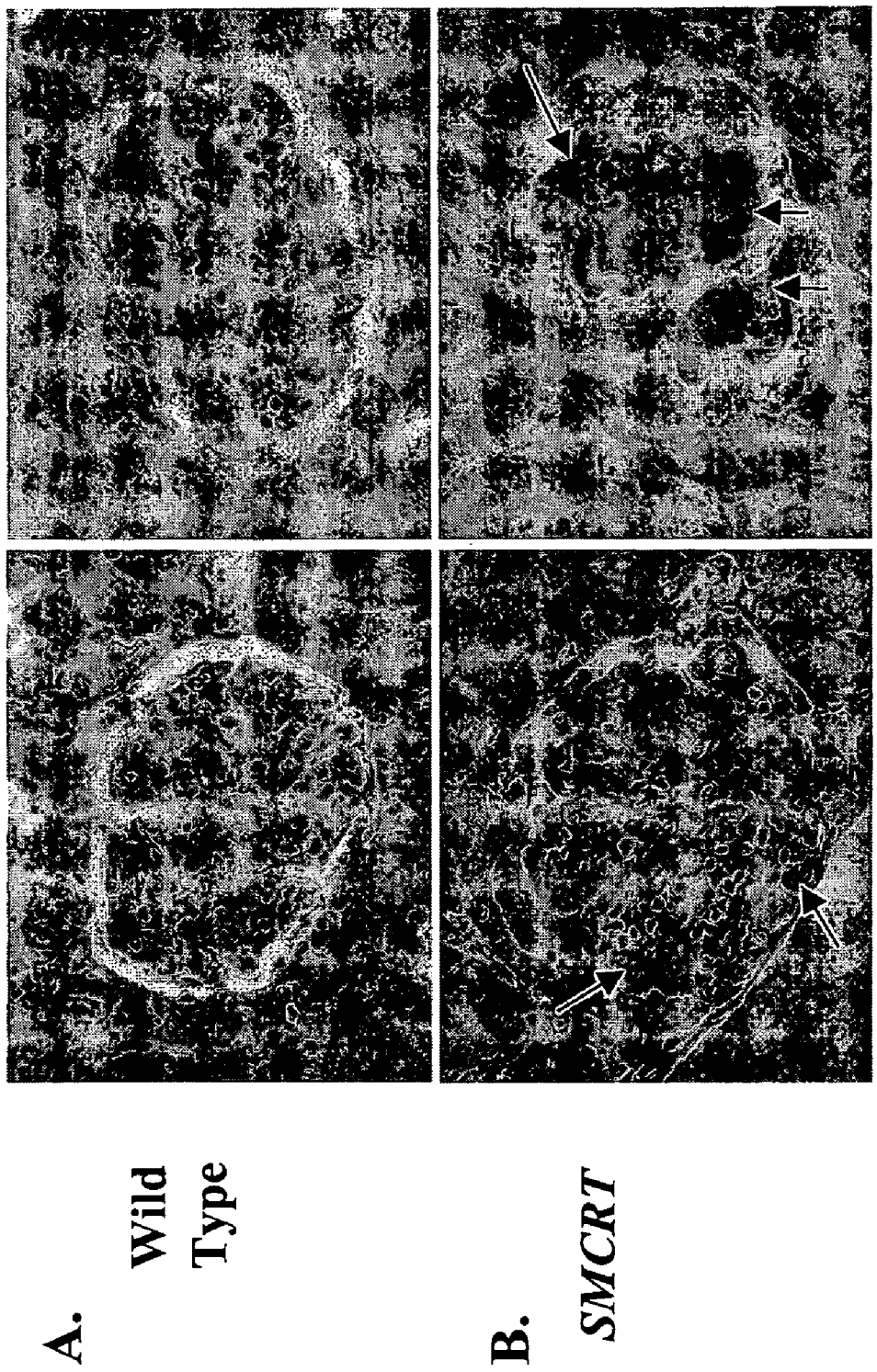
FIG. 7. Histological structure of the kidney glomeruli from wild type (A) and a SMCRT mouse (B). Arrows in B point to accumulation of blood in the glomeruli of the kidney of the SMCRT mice. This could be due o formation of thrombus in the glomerulus of the kidney.

SMCRT transgenic mice—A truncated SM22α promoter (1343 base pairs of the 5' flanking region) which has been shown to target the Lac Z reporter gene expression in the vascular smooth muscle cells (specifically in the arterial side) but not other smooth muscle cells in the mouse embryo (Li et al., 1996) was used. We obtained this promoter from Dr. E. Olson (Southwestern Medical Centre, University of Texas, Dallas, USA) and cloned it upstream of mouse CRT cDNA tagged with HA epitope (HA-CRT). The epitope tag was used to differentiate between the expression of the transgene and the endogenous CRT. However, as will be appreciated by one of skill in the art, any suitable tag known in the art may be used if so desired. This plasmid was then used to generate a transgenic mouse overexpressing HA-CRT (SMCRT) in the vascular smooth muscle cells. The genotype of these mice was confirmed by PCR of the genomic DNA with primers specific to the sequence of SM22α (5' primer) and CRT (3' primer). The expression of the HA-CRT in these mice was detected using western blot with a polyclonal antibody to HA (FIG. 2). The heterozygous SMCRT mice develop abnormalities at an adult stage (about 4–10 months old). The older mice become lethargic and inactive. Most of the male heterozygous animals develop skin lesions (FIG. 3) and hemangioma which can be detected on the skin. These mice suffer from lung congestion (FIG. 4) and kidney thrombosis (FIG. 5), symptoms resembling congestive heart failure. The evidence of heart failure is also observed in older (10–12 months) female heterozygous mice. Analysis of the kidney of the SMCRT mice showed hemorrhage from renal vessels in the renal adipose tissue and the presence of thrombus inside the kidney capsules (FIG. 5A, C). Histological analysis of the kidneys from the mice at end stage disease showed necrosis in the kidney medulla and cortex (FIG. 6B, C). There was also increased blood accumulation in the kidney glomeruli (FIG. 7B) of the SMCRT mice as compared to the wild type glomeruli (FIG. 7A). This could result in thrombosis in glomeruli. Histological analysis (Hematoxylin/Eosin) of the lungs of these mice we have seen congestion of the lungs and accumulation of blood in the alveoli (FIG. 4).

Figure 8:
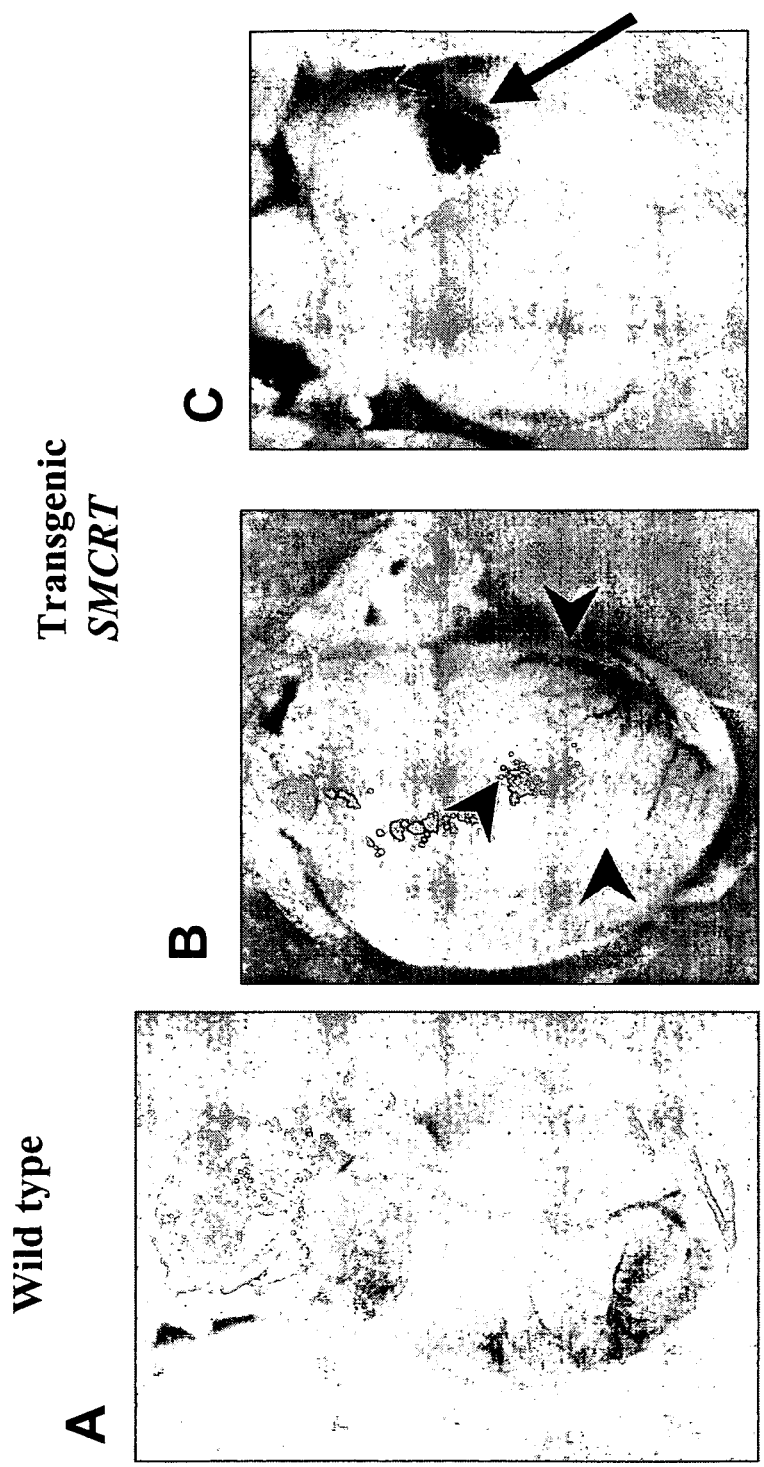
FIG. 8. Heart and coronary artery structure in (A) wild type and (B, C) transgenic mice overexpressing calreticulin in the vascular smooth muscle cells (SMCRT). (A) and (B) are hearts freshly isolated from age-matched mice, while the heart in (C) is a picture from a formalin preserved heart. In the SMCRT hearts there is an increased coronary artery vascularization (arrowheads in B). The SMCRT hearts were also dilated as compared to wild type hearts. As seen in (C) we also observed ruptured coronary artery in some of the hearts from end stage of disease (mouse were dying) (Arrow in C).
Figure 9:
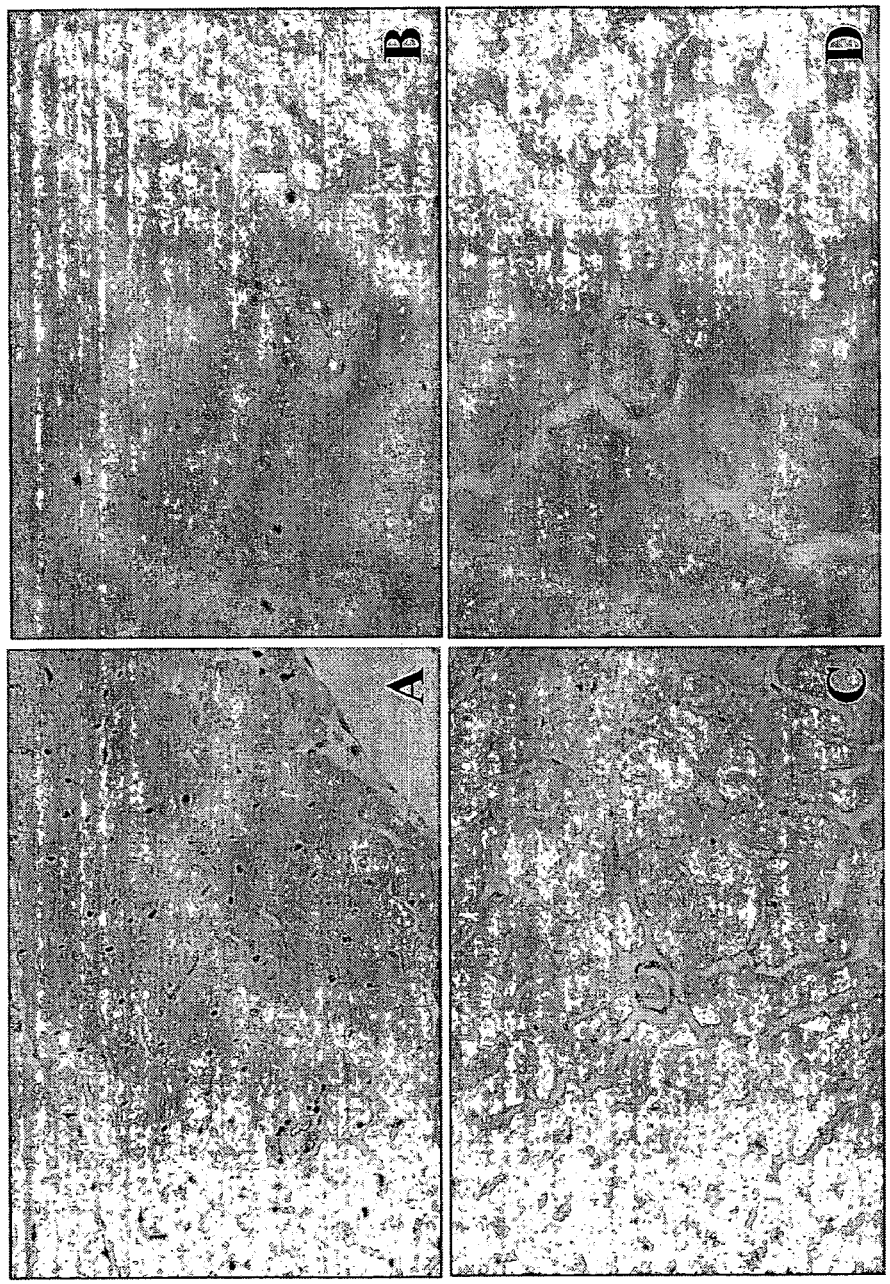
FIG. 9. Histological section from a papillary muscle in the heart of wild type (A, B) and SMCRT transgenic mice (C,D). A and C are at 20× magnification while B and D are at higher magnification (40×). The SMCRT heart muscle (C,D) shows increased interstitial spaces between the muscle fibers and around the coronary artery when compared to the wild type heart muscle (A,B).
Figure 10:
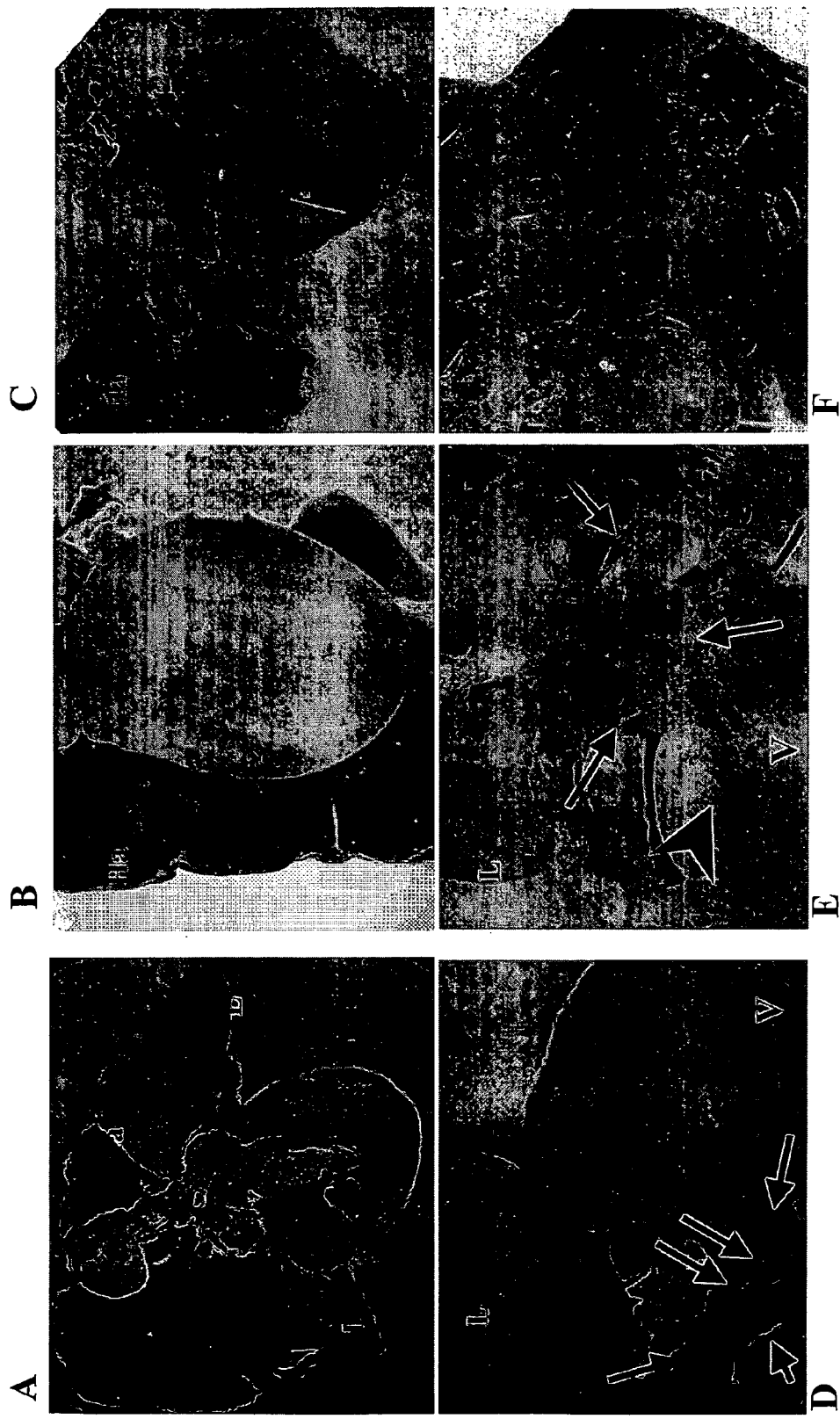
FIG. 10. Giant hemangioma associated with the hearts isolated from two different lines of transgenic mice overexpressing calreticulin in the vascular smooth muscle cells (SMCRT) (B,C). A and B are images of the same heart showing the size of the hemangioma. This structure appears in all the SMCRT mouse lines we have (4 different lines). It increases in size by age. The heart in (C) was isolated from one SMCRT mouse before it showed the symptoms of heart failure, and the picture was taken from freshly isolated tissue. Arrows in (D) and (E) show the origin of this hemangioma to be from the aorta (in two different heart). Arrowhead in (E) points to the dilated coronary artery in this heart. F) shows a higher magnification of this structure. All tissues in (A, B, D and F) were preserved in formalin. L=Lung, Ha=Hemangioma, V=ventricle FIG. 11. Histology of the giant heamangioma (hemangioendothelioms) shown in FIG. 10F. (A, B, C, D) show different cell types found in the lumen of this tumor. Arrow heads in (A), (B) and (D) show cells which look more like epithelial cells, while the arrow head in C show other cell type which resemble mesenchymal cells. The blue arrows in A,B, and C show the red blood cells which is also part of this tumor. The surface of this tumor is covered with a single layer of cells resembling endothelial cells (Arrows in E and F). This hemangioendothelioma also contains lumen likestructures (D) which are lined by endothelial-like cells (arrows in D).

There are also defects in the heart of the SMCRT mice including: heart dilation, increased vascularization of the coronary arteries and rupture of coronary artery in some of these mice (FIG. 8). We also observed changes in the ultrastructure of the myocardium (FIG. 9) with increased interstitial spaces. However, the major defect in these mice is the presence of Giant hemangioma in the chest (FIG. 10). The giant hemangioma originates from the base of the aorta (FIGS. 10D and E). We have 4 different lines of the SMCRT transgenic mice and all four develop the giant hemangioma. The overall symptoms of these mice are similar to the Kasabach-Merritt Syndrome, the pathology of which includes: giant hemangioma with consumptive coagulopathy disseminated intravascular coagulation, and congestive heart failure. The Kasabach-Merritt Syndrome is more common in female infants. However, in the SMCRT mice the earliest evidence for the development of hemangioma we observed was at 3 months old male mice. Recently, Kasabach-Merritt Syndrome has been associated with two distinct vascular tumors: the Kaposiform hemangioendothelioma and tufted angiomas (Enjolras et al., 1997). Tufted angioma is a benign slow growing angioma found in young patients which is localized to the skin and subcutaneous tissue (Jones and Orkin, 1989). The Kaposiform hemangioendothelioma is an aggressive vascular tumor which can occur in soft tissue of the trunk, extremities and retroperitoneum (for review see Gampper and Morgan, 2002). The hemangioendothelioma occurs with similar frequency in both sexes and can develop at birth or later in life (Gampper and Morgan, 2002). This vascular tumor is associated with a high mortality rate and treatment is often inadequate (Powell, 1999). The histopathology reports on the Kaposiform hemangioendothelioma show that this tumor is surrounded by a thin-walled vessel lined by endothelial cells and filled with erythrocytes, thrombus, and sheets of cells (epithelioid and mesenchymal) (Perkins and Weiss, 1996). The molecular mechanism of development of the hemangioendothelioma is not known.

Figure 11:
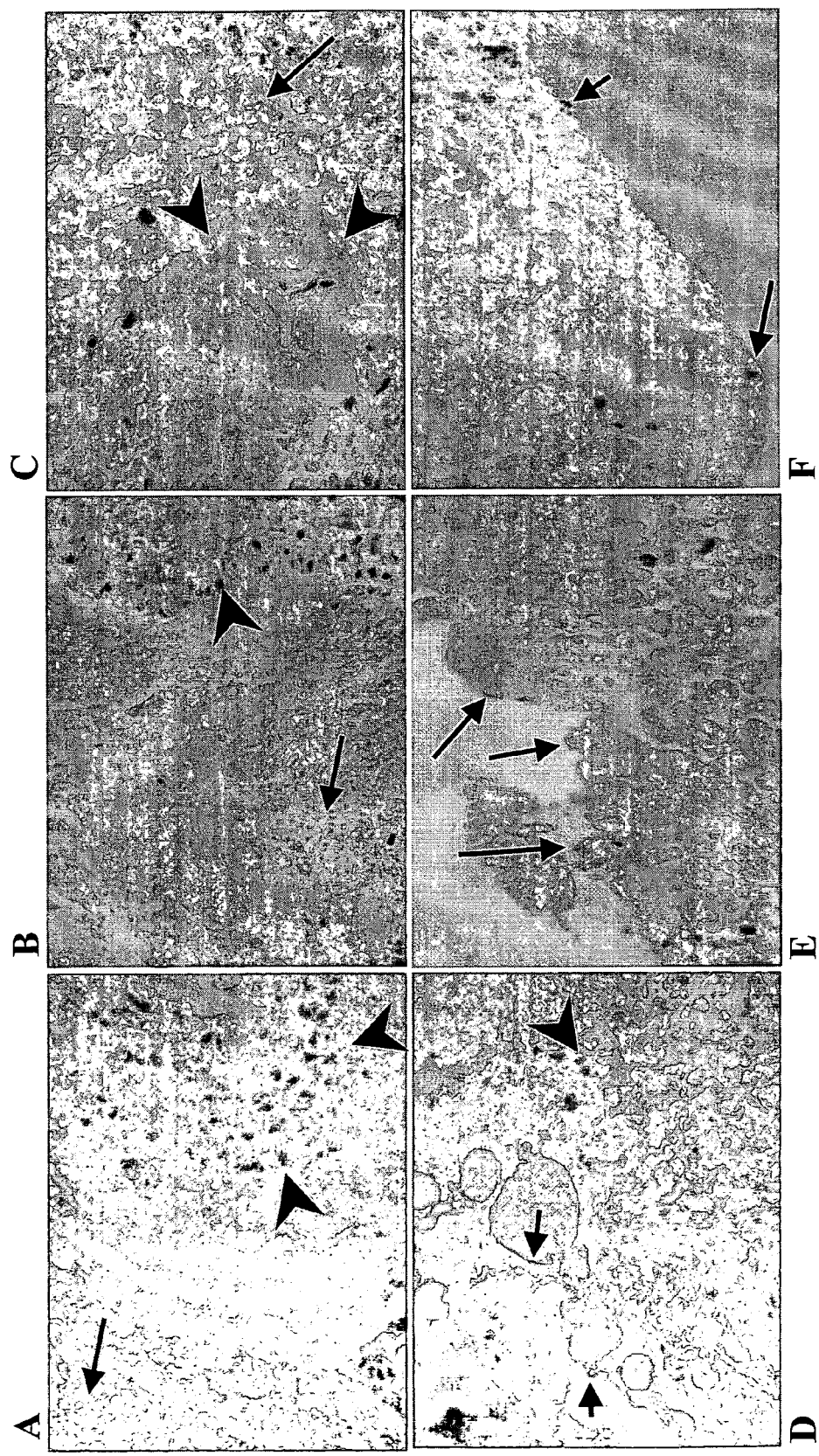
Figure 12:
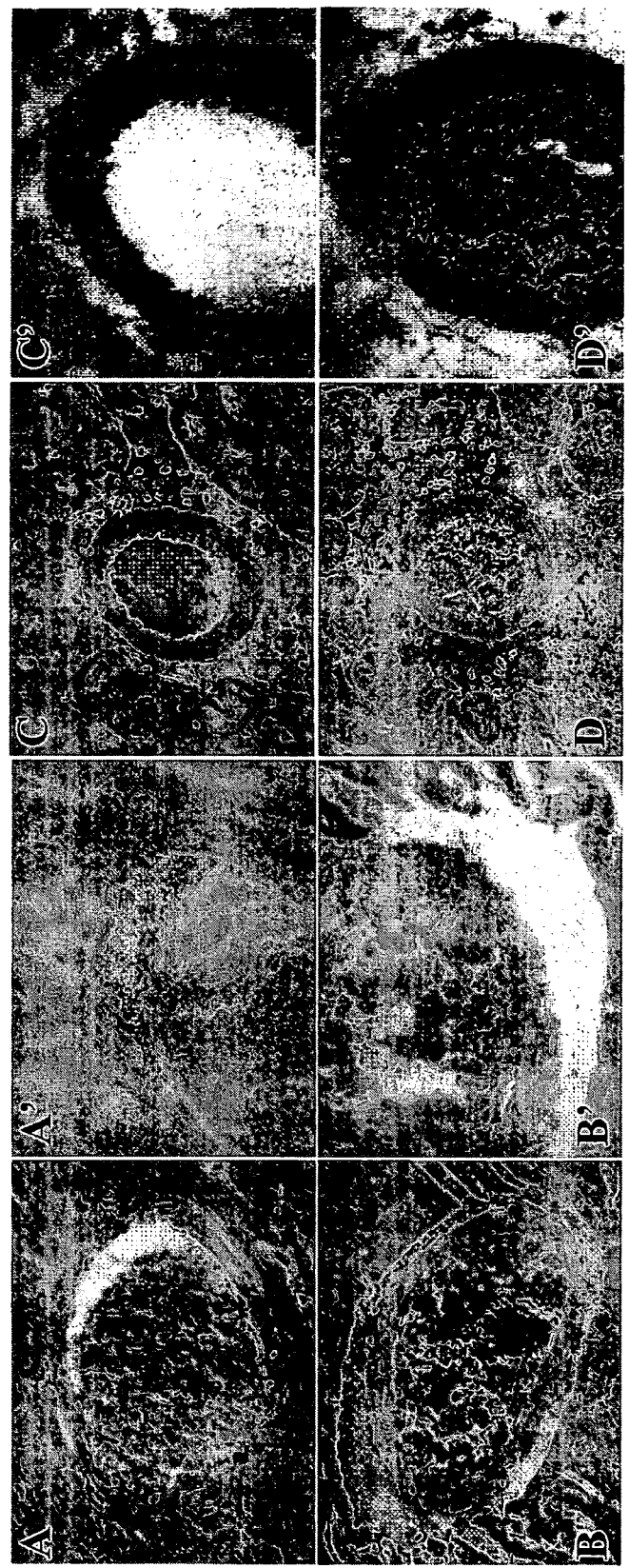
FIG. 12. Histological structure of coronary artery (A, A', B, B') and a kidney arteriole (C, C', D, D'). The upper panel (A, A' and C, C') are from a wild type mouse and the lower panel (B, B', C, C') are from a SMCRT mouse. As seen in (B, B') there is a larger interstitial space between the coronary artery and the myofibers in the SMCRT mouse as compared to the wild type (A,A'). The same can also be seen in the kidney arteriole from the SMCRT mouse compared to the wild type. Higher magnification images of the arterial walls (A', B', C', D') show some changes in the structure of the vessel wall. To understand the nature of these changes we will use immunohistochemistry to analyze the expression of the extracellular matrix proteins.
Figure 13:
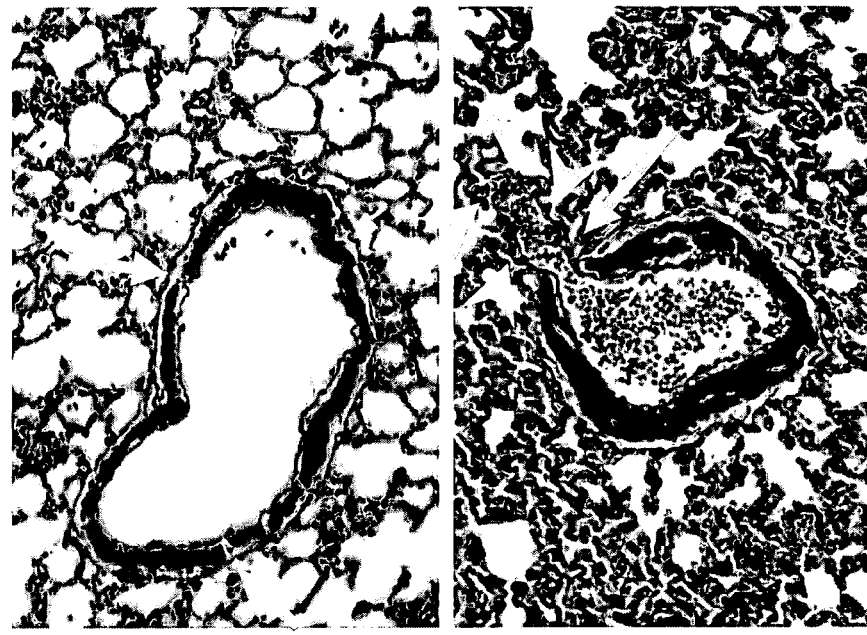
FIG. 13—Masson Trichrome staining of lung sections of wild type (A) and SMCRT (B), showing the changes in the arteriole walls of the transgenic mice. Arrows (Green) indicates the disruption in the smooth muscle layer and migration of the endothelial cells thus developing a pouch containing red blood cells (lined by the arrow heads in B) which can lead to the formation of hemangioma.
Figure 13:
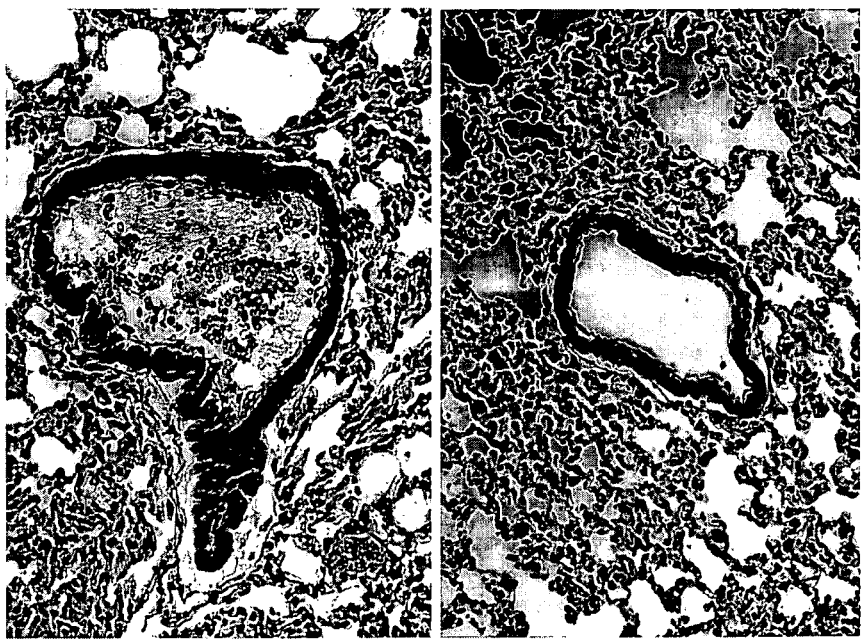

Histological analysis (Hematoxylin/Eosin) of the hemangioendothelioma isolated from the heterozygous SMCRT mice (FIG. 11) shows the presence of a vessel like structure covered with a layer of cells resembling endothelial cells (FIG. 11E, F). We also observed the appearance of several lumen-like structures inside this tumor which is also lined with endothelial-like cells (FIG. 11D). The presence of blood cells (blue arrows in FIGS. 11A, B and C) and different types of cells (resembling epithelial cells, Arrow head in FIG. 11A, 11B, 11D and mesenchymal cells Arrow head in FIG. 11C) were also detected. Histological sections of coronary artery (FIG. 12A) and kidney arteriol (FIG. 12B) shows an increase in the connective tissue around these vessels and changes in the structure of the smooth muscle layer of these vessels. The increased expression of CRT in the vascular smooth muscle cells results in the disruption of the smooth muscle layer (FIG. 13B, C). These changes lead to activation of the endothelial cells to proliferate and migrate through the smooth muscle cells (FIG. 13C) resulting in the formation of hemangioendothelioma. The observed defects in the SMCRT mice indicate vascular wall remodelling which could cause the increased permeability of blood vessels in the SMCRT mice. Also the presence of such a large tumor in the vascular system can cause changes in the intravascular pressure (leading to hypertension) which can also result in some of the observed defects. Indeed one case report showed the development of hemangioendothelioma from thoracic aorta of a 54 years old woman which led to aortic obstruction, hypertension and congestive heart failure (Traverse et al., 1999). Therefore, we will study changes in blood pressure in these mice. The SMCRT mouse is a unique mouse model which is proving very interesting and to our knowledge is the only animal model for the hemangioendothelioma.

To identify all the cell types involved in the formation of this tumor we will use cell specific antibodies for immunohistochemical staining. We will isolate the tumor and areas of the skin with hemangioma from the SMCRT mice. This tissue will be fixed in 4% paraformaldehyde and processed for freezing in Tissue Tec as described previously (Mesaeli et al., 1999). Thin cryosections (7–10 μm) will then be prepared and incubated with the following antibodies: CD31, CD34 (BD Biosciences) and von Willebrand factor (Dako) as endothelial markers, smooth muscle actin (Sigma), vimentin as mesenchymal cell marker (Chemicon) and RTU-ESA (Vector Laboratories) as epithelial specific marker. This staining will be followed by FITC (or Texas red) labeled secondary antibodies. The nuclear stain DAPI will be used to localize the nuclei in each section. The confocal images from the FITC (or Texas red) signal and DAPI will then be superimposed to study the localization of the cells. We are using three different markers for endothelial cells because previous report has showed variability in the expression of these endothelial markers in the hemangioendothelioma (Mentzel et al., 1997).

Our observation of the accumulation of blood in the kidney glomeruli and lungs implies an increase in the permeability of the vasculature in the SMCRT mice. Therefore, to test for the changes in the microvascular permeability in different tissues we will use fluorescently labeled albumin following the protocols described previously (Harris et al., 2002). We will label albumin (Sigma) with FITC using the FluoroTag FITC Conjugation kit (Sigma). In brief, albumin (10 mg/ml) and FITC powder will be dissolved in carbonate-bicarbonate buffer. The FITC solution will be added slowly to the BSA and mixed for 2 hrs. The FITC-BSA conjugate will be separated from the free FITC by a G25 column. I have used this system previously for FITC labeling of CRT (Dai et al., 1997). The FITC-albumin or FITC alone will be injected in the tail vein of the transgenic SMCRT and non-transgenic litter mate mice. After 30 min (Harris et al., 2002), these mice will be euthanized, lung, kidney, skin and heart will be collected and fixed for 10 min in 4% paraformaldehyde followed by freezing. Thin cryostate sections (6–10 μm) will be generated. These sections will be mounted in a mounting media containing DAPI (a nuclear marker) to localize the cell nuclei. The fluorescence in these sections will then be analyzed. If there is an increase in vascular permeability we should see the FITC-albumin conjugate in the extravascular spaces.

One of the pathological diagnoses associated with hemangioendothelioma is disseminated intravascular clotting associated with thrombocytopenia (decreased platelet count in circulating blood). Decreased levels of platelets, procoagulant proteins and protease inhibitors is the result of activation of the coagulation, degradation of coagulation factors accompanied by decreased synthesis of these factors. As shown in FIG. 5, 8, 9 we have observed an increase in the thrombus formation in different tissue of the SMCRT mice. Thus it is important to examine the changes in the blood clotting and factors involved in this process in these mice. We will examine CBC (blood cell count, and morphology), platelet counts, clotting time and hematocrit values. Furthermore, we will test the platelet aggregation characteristics in platelet rich fraction of blood from the SMCRT and wild type mice. If we find changes in the platelet aggregation we will then evaluate the expression level of different proteins involved in the blood clotting pathway. We will use western blot analysis to test the level of fibrinogen, thrombin, Factor VIII and X. These tests will help us to identify the mechanism resulting in formation of thrombus in different tissues.

To date all of the samples we analyzed were isolated from adult mice with fully developed disease or at end stage. Because in human this disease can also be found at an early age (found from 6 months to 74 years of age) (Gampper and Morgan, 2002; Powell, 1999), we will determine when this tumor starts developing in the SMCRT mice. Thus we will carry out an age dependent study. In these studies we will use mice at different age starting from late embryonic age (E17 and E19), neonate (2 days), 1, 5 and 8 months old SMCRT mice. These mice will be first checked for the appearance of skin changes. They will then be euthanized and tumor, heart, major arteries (aorta, thoracic artery, and renal artery), lung and kidneys will be used for histological analysis.

Figure 14:
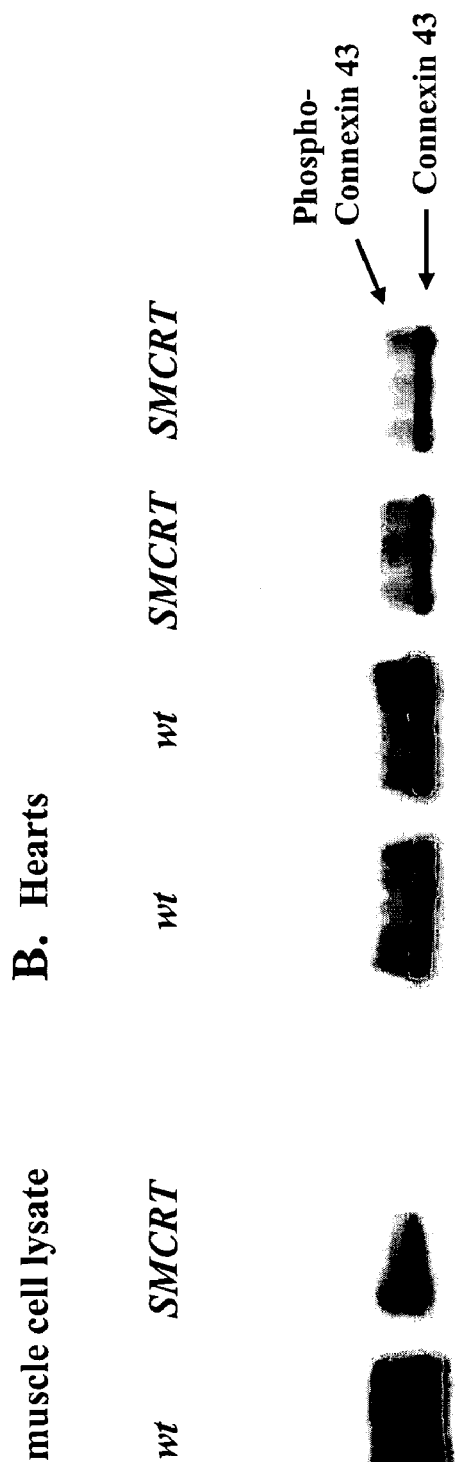
FIG. 14—Western blot analysis showing connexion 43 expression in the vascular smooth muscle cells (A) and hearts (B) isolated from the wild type and SMCRT mice. There was a significant decrease in the connexion 43 protein in the transgenic mice as compare to the wild type mice.

A summary of the possible mechanisms for the development of hemangioendothelioma in the SMCRT mice is outlined in FIG. 1. In the arterial wall of these mice the vascular smooth muscle cells (VSMC) are overexpressing CRT, while the endothelial (and other cells) have their basal expression of CRT. In the vessel wall, there is a dynamic interaction between the VSMC and the endothelial cells through the basement membrane which is made predominantly from collagen IV, laminin and heparan sulfate proteoglycans. A second layer of ECM known as interstitial matrix and is made from fibrillar collagen and fibronectin surrounding the VSMC and pericytes. Any change in the composition of these ECM will disturb the vessel wall structure. In the SMCRT vessel wall, the changes in the VSMC can be on multiple levels. We postulate a change in the composition of the ECM surrounding the VSMC cells due to either their decreased expression or increased degradation by active proteases. Indeed, overexpression of CRT has been shown to increase the secretion and activation of pro-MMP2 protein (Ito et al., 2001). CRT has also been shown to bind glycosylated laminin in the ER (McDonnell et al., 1996) perhaps affecting its folding. Previously we have showed that overexpression of CRT results in increased cell spreading and adhesion (Opas et al., 1996; Fadel et al., 1999). Thus we anticipate an increased expression of adhesion proteins in the VSMC causing them to attach to the ECM and spread. Loss of cell-cell contact proteins in VSMC can result in an increased permeability of the vessel wall. Gap junctions are one of the means of cell-cell contacts between the VSMC and endothelial cell (Little et al., 1995; Xia et al., 1995). Connexin 37, 40 and 43 are the main gap junction proteins present in both VSMC (Arensbak et al., 2001; Cai et al., 2001; van Kempen and Jongsma, 1999) and endothelial cells (Delorme et al., 1997; Simon and McWhorter, 2002; van Kempen and Jongsma, 1999). A recent report by Nakamura et al., (Nakamura et al., 2001a) showed that overexpression of CRT in the heart results in a significant decrease in the expression of connexin 40 and 43 in the cardiomyocytes. Indeed, we observed a significant decrease in the connexion 43 expression in vascular smooth muscle cells derived from the descending aorta (FIG. 14A) and in the hearts (FIG. 14B) of the SMCRT mice as compared to the wild type. Decreased connexin expression in the VSMC can result in altered communication via gap junction between the VSMC and endothelial cells thus affecting their function.

The endothelial cells of the SMCRT vessel wall express basal level of CRT and according to the above predicted changes they are faced with a change in the ECM. Changes in the ECM have been shown to induce endothelial cell to release growth factors (Dvorak et al., 1995), thus increasing the rate of endothelial cell proliferation (Underwood et al., 1998) and migration (Seeger et al., 2002). Collectively the changes in the ECM and the endothelial layer of the vessel wall activate platelet adhesion to the vessel wall (Balleisen and Rauterberg, 1980) leading to platelet aggregation and blood clotting. Evidence of thrombus formation in different tissues of the SMCRT mouse (tumor, kidney and lung) has been observed. Adhesion of platelets to the vessel wall and formation of fibrin (by breakdown of fibrinogen) in the blood clot will also result in release of growth factors (Campbell et al., 1999; Tezono et al., 2001) in this site leading to increased endothelial cell proliferation and migration. This further activates the angiogenic process and formation of the tumor in these mice.

We are studying the mechanism of development of this tumor (hemangioendothelioma) with emphasis on role of CRT in the development of this disorder. It is known that hemangioendothelioma develops as a result of biphasic proliferation and migration of endothelial cells to form dilated vessels which is filled with erythrocytes, thrombus with latter invasion of epithelioid and mesenchymal cells (Perkins and Weiss, 1996). One of the mechanisms that overexpression of CRT in smooth muscle cells can lead to the vascular wall changes which cause the development of this tumor could be via altering the expression of the extracellular matrix (ECM) and adhesion molecules rendering the vessel walls leaky. The change in the local composition of ECM in-vessel wall in addition to the shear force in the vessel wall has been shown to govern the ability of the endothelial cells to proliferate, migrate, differentiate and/or undergo apoptosis (Reviewed in Ingber, 2002). In the SMCRT mice the development of hemangioendothelioma depends on the abnormal cell growth and migration. Using histological techniques (Masson Trichrome, FIG. 13B, C) we observed that the increased expression of CRT in the vascular smooth muscle cells leads to changes in this layer of the vessel wall leading to activation of endothelial cell proliferation and migration (FIG. 13C arrow). These changes in the endothelial cells could be the cause of development of hemangioma and increased angiogenesis observed in the SMCRT mice.

Collagen (types I, III and IV) and elastin (mainly present in resistant arteries) are the major protein component of the ECM in the vessel wall (van der Rest and Garrone, 1991; Rosenbloom et al., 1993). Thus, in the initial experiments we will stain the paraffin embedded sections of different tissues of SMCRT and wild type mice with Van Gieson's Picric Acid stain to determine the changes in the collagen deposit in the microvasculature of different tissues. To detect the elastic fibers we will use the Elastic Stain (Sigma) which is a hematoxylin based stain. Staining of the paraffin sections will enable us to obtain good histological (and ultrastructural) details. Second, we will determine the temporal and spatial expression of ECM proteins including: elastin, collagen (I, III and IV), fibronectin, and laminin in the vessel walls of the SMCRT mice. Western blot with antibodies (available from Chemicon and Calbiochem) to these specific proteins will be carried out on tissue homogenates from arteries, veins, myocardium, lung, kidney and the tumor. We will also carry out immunohistochemical staining of the SMCRT and wild type tissue sections with antibodies to ECM proteins. Tissues (listed above) will be fixed in 4% paraformaldehyde, embedded and frozen (as described in Mesaeli et al., 1999), then 10–15 μm cryostat sections will be cut. The sections will be stained with antibodies to collagen I, III, IV, laminin, fibronectin, (available from Sigma and Chemicon) followed by staining using Vectastain Elite ABC kit and Vector DAB substrate (Vector Labs Inc.). The nuclei will be counter stained with methylgreen or hematoxylin for ultrastructural determination.

Figure 15:
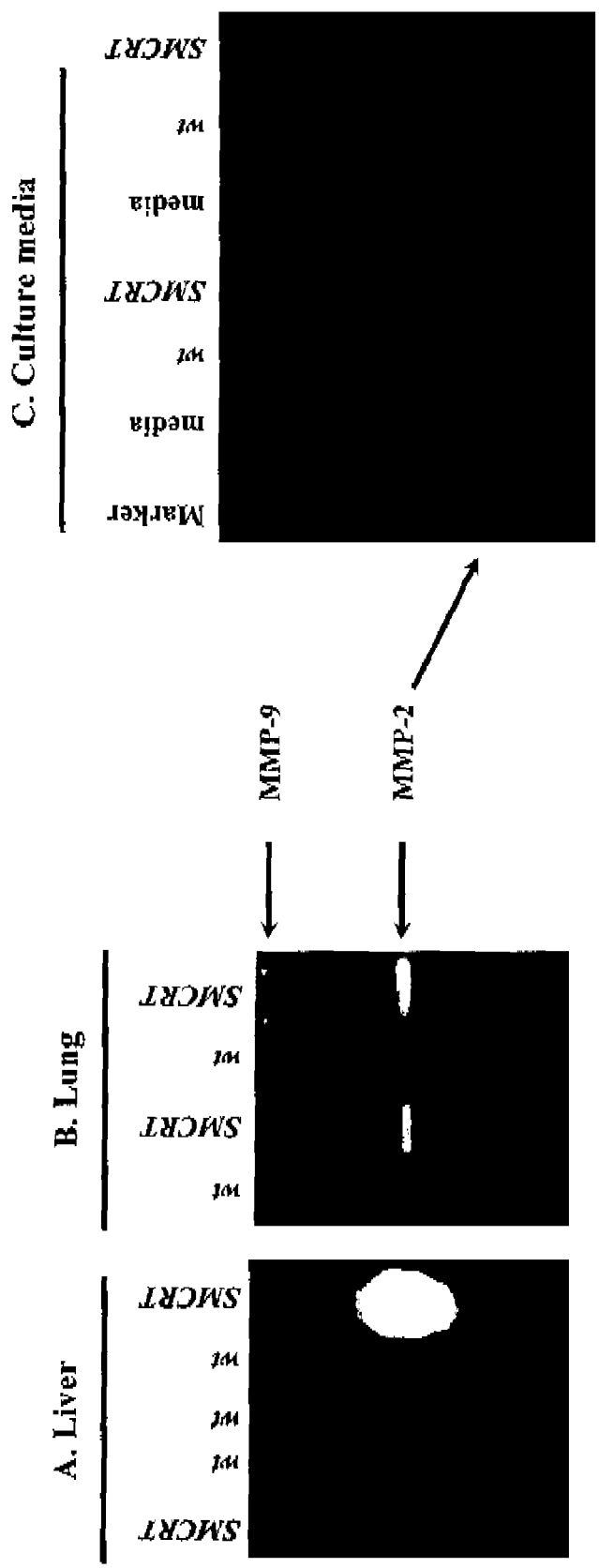
FIG. 15. Gelatin Zymography detecting the MMP-2 and MMP-9 activity in liver (A) and lung (B) tissue isolated from the wt and SMCRT mice. C) shows the activity of MMP-2 in the culture media from the wt and SMCRT smooth muscle cells detected by gelatin zymography. Briefly, cells were cultured in DMEM containing Insulin and transferrin for 24 hrs. 30 µl of media from culture plate with no cells (Media), wt cells and SMCRT cells (or 30 µg protein from each tissue) were separated on 7.5% SDS-acrylamide gel containing 1 mg/ml Gelatin. After removal of SDS from the gel (to re-nature the proteins), it was incubated in zymography buffer overnight at 37° C. The gels were then stained with Coomassie Blue and de-stained. The white bands represent the activity of MMP in the sample.

The changes in the ECM are not only limited to changes in their expression, but also to the rate of turnover of these proteins. The turnover of ECM is essential for many processes including embryonic development, wound healing, tissue remodeling, and disease development (such as cancer and vascular disease). The turnover of ECM is mediated by the activity of different proteases including secreted matrix metalloproteinase (MMP). Because of the important function of MMPs in regulating cell migration and invasion, all the MMP are secreted as an inactive pro-MMP. A large number of MMP has been identified in different tissues, however only MMP-1, 2, 3, 7 and 9 have been reported in vascular tissue (Jacob et al., 2001). MMP-1 is a collagenase which is secreted by endothelial cells (Lin et al., 1997). MMP-2 and MMP-9, which are gelatinases, are secreted by endothelial and vascular smooth muscle cells (Gurjar et al., 1999; Ishii and Asuwa, 2000; Peracchia et al., 1997). MMP-7 is an elastase and has a low level of expression in the vascular wall (Jacob et al., 2001). The activities of these MMPs are tightly regulated by tissue inhibitor metalloproteases (TIMP). Four isoforms of TIMP have been found, TIMP-1 binds pro-MMP-9, TIMP-2 and -4 bind pro-MMP-2 (Brew et al., 2000). Therefore, we will examine for changes in the activity and the expression of MMPs and TIMPs in the arterial walls of the SMCRT mice and compare that to their wild type litter mate. In our preliminary data on MMP activity we used zymography techniques. As shown in FIG. 15A, the activity of both MMP-2 and MMP-9 are increased in the tissues isolated from the SMCRT mice as compared to wild type. In addition, we observed an increase in the MMP-2 activity in the primary smooth muscle cells isolated from the descending aorta from the transgenic mice as compared to the wild type mice (FIG. 15 B). To determine if these changes in the MMP activity is due to changes in the protein expression or a decrease in the TIMP level we will quantifying the expression of MMP-2, -9 and TIMP-1, -2, -4 using western blot analysis and specific antibodies to these proteins (Calbiochem). If there were changes in the protein levels, we will determine if these changes are due to an increase in the mRNA level using quantitative RT-PCR. We will also determine the cellular localization of these proteases using immunohistochemical techniques (as described above). Interestingly, Ito et al. has recently showed that overexpression of CRT in human rhabdomyosarcoma cells resulted in an increase in the secretion and activation of pro-MMP2 (Ito et al., 2001). However, no data is available on other MMP or TIMP expression or the activity of any of these proteases when the expression of CRT is altered. Therefore, we propose to study the activity of MMP-2 and MMP-9 in the serum and in the media from the primary vascular smooth muscle cell cultures isolated from the SMCRT and wild type mice. One disadvantage of using cultured VSMC is that these cells in culture undergo phenotypic changes. However, we are interested to measure the release of the MMP proteins from the VSMC layer only not the whole artery. Therefore, to avoid this setback we will only use the first passage of these cells (as we have done in FIG. 15B). In our experiments we have isolated vascular smooth muscle cells (VSMC) from the descending aorta of the SMCRT and wild type mice using explant techniques. Because the MMPs are secreted from the cells we will separate the media from these VSMC to test for their activity. We will also harvest serum from the SMCRT and wild type mice to test for MMP activity. The MMP assay (available from Chemicon) utilizes a biotinylated gelatinase substrate which is cleaved by the active MMP-2 or MMP-9. The remaining biotinylated fragments are then measured in a colorimetric ELISA based assay using a biotin-strepavidin complex.

Cell migration is essential during vascular development and vascular injury (Noden, 1988; Poole and Coffin, 1989). Once endothelial cells differentiate, they proliferate and migrate and assemble to generate the vascular network. Cell migration is also important in recruiting the smooth muscle cells to the endothelial tubes for maturation of the blood vessel. Endothelial cell migration is also important in branching of the vessels during the process of wound healing (Reidy and Schwartz, 1981) and in tumor angiogenesis (Sheu et al., 1997). In the development of hemangioendothelioma, endothelial cells and other cells (erythrocytes, epithelial and mesenchyme cells) have to migrate to form the tumor (Gampper and Morgan, 2002). How is this migration initiated? As outlined in FIG. 1, we propose that in the vessel wall of the SMCRT mice, the ECM structure is altered (perhaps by a decrease in the synthesis or accelerated degradation of ECM fibers). In these vessels, the endothelial cells (express only the endogenous level of CRT) will have less substrate (ECM) to adhere to thus promoting their migration, while VSMC will be more adherent and will not follow the migratory path of the endothelial cells. Indeed, previously we showed that overexpression of CRT renders the cells more adherent while decrease in CRT expression in these cells (using antisense oligo) resulted in less adhesion (Fadel et al., 1999). We also showed that overexpression of CRT in cultured cells increases the expression of vinculin and N-cadherin (adhesion proteins) (Opas et al., 1996). The SMCRT mouse model would be ideal to test the expression of different adhesion molecules in two different cell types expressing different levels of CRT. Here, we propose to measure the expression (by western blot) and localization (by immunohistochemistry) of different adhesion molecules including: integrins ($\alpha_2\beta_1$, $\alpha_v\beta_3$ and $\alpha_3\beta_1$), vinculin, and cadherins in the vascular wall of the. SMCRT mice as compared to the wild type mice. To study cell migration, we will isolate smooth muscle cells from the SMCRT and wild type mice as described above. The rate of cell migration will be tested using Boyden chambers containing filters with a pore diameter of 8 μm (Costar, as described in Dai et al., 1997). Cell suspensions will be plated in the upper part of the chamber and incubated at 37° C. for 2–8 hours. The cells that migrate into the filters will be fixed, stained with Giemsa dye and counted. To test the effects of different ECM proteins (collagen, fibronectin, laminin) on the rate of cell migration, the wells will be coated with different substrates and the above experiments will be repeated.

To study the changes in the rate of cell proliferation in arterial wall and tumor in situ we will use bromo-2'-deoxyuridine (BrdU) to label newly synthesized DNA. Wild type and SMCRT mice will be injected intraperitoneally with 0.2 ml of 15 mg/ml BrdU (Roche Diagnostics) dissolved in 0.86% saline (Wigle et al., 1999). 2 hrs after injection these mice will be euthanized. We will harvest the tumor and the major thoracic arteries from the SMCRT mice, as a control we will isolate the major thoracic arteries from the wild type mice. These tissues will be fixed in 4% paraformaldehyde (PFA), frozen and cryosectioned. The sections will be denatured with 2N HCl and re-natured in 0.1M Sodium Borate buffer pH 8.5 to denature DNA (Wigle et al., 1999). Sections will then be stained with monoclonal antibody to BrdU (BD Biosciences) and visualized with a FITC-secondary antibody. To determine if there is a cell specific difference in the cell proliferation we will use cell specific antibodies as markers to double label the tissue sections. We will use anti-CD31, CD34 (BD Biosciences) and von Willebrand factor (Dako) as endothelial cell markers, and anti-smooth muscle actin (Sigma) for smooth muscle cells. Each antibody will be visualized by using a Texas-Red conjugated secondary antibody.

While the preferred embodiments of the invention have been described above, it will be recognized and understood that various modifications may be made therein, and the appended claims are intended to cover all such modifications which may fall within the spirit and scope of the invention.

REFERENCES

Ahmadi, S., E. Kardami, M. Michalak, and N. Mesaeli. 2002. Altered connexin 43 localization in calreticulin knockout mice. *Mol. Biol. Cell.* 13:1209.

Arensbak, B., H. B. Mikkelsen, F. Gustafsson, T. Christensen, and N. H. Holstein-Rathlou. 2001. Expression of connexin 37, 40, and 43 mRNA and protein in renal preglomerular arterioles. *Histochem Cell Biol.* 115:479–87.

Ausprunk, D. H., S. M. Dethlefsen, and E. R. Higgins. 1991. Distribution of fibronectin, laminin and type IV collagen during development of blood vessels in chick chorioallantoic membrane. *Issues Biomed.* 14:93–108.

Baksh, S., and M. Michalak. 1991. Expression of calreticulin in *Escherichia coli* and identification of its Ca2+ binding domains. *J Biol Chem.* 266:21458–65.

Balleisen, L., and J. Rauterberg. 1980. Platelet activation by basement membrane collagens. *Thromb Res.* 18:725–32.

Bar, T. 1980. The vascular system of cerebral cortex. *Adv. Anat. Embryol. Cell Biol.* 59:1–62.

Bastianutto, C., E. Clementi, F. Codazzi, P. Podini, F. De Giorgi, R. Rizzuto, J. Meldolesi, and T. Pozzan. 1995. Overexpression of calreticulin increases the Ca2+ capacity of rapidly exchanging Ca2+ stores and reveals aspects of their lumenal microenvironment and function. *J Cell Biol.* 130:847–55.

Bogers, A. J., A. C. Gittenberger-de Groot, R. E. Poelmann, B. M. Peault, and H. A. Huysmans. 1989. Development of the origin of the coronary arteries, a matter of ingrowth or outgrowth? *Anat Embryol.* 180:437–41.

Brew, K., D. Dinakarpandian, and H. Nagase. 2000. Tissue inhibitors of metalloproteinases: evolution, structure and function. *Biochim Biophys Acta.* 1477:267–83.

Brooks, P. C., R. A. Clark, and D. A. Cheresh. 1994a. Requirement of vascular integrin alpha v beta 3 for angiogenesis. *Science.* 264:569–71.

Brooks, P. C., A. M. Montgomery, M. Rosenfeld, R. A. Reisfeld, T. Hu, G. Klier, and D. A. Cheresh. 1994b. Integrin alpha v beta 3 antagonists promote tumor regression by inducing apoptosis of angiogenic blood vessels. *Cell.* 79:1157–64.

Burns, K., B. Duggan, E. A. Atkinson, K. S. Famulski, M. Nemer, R. C. Bleackley, and M. Michalak. 1994. Modulation of gene expression by calreticulin binding to the glucocorticoid receptor. *Nature.* 367:476–80.

Burri, P. H., and M. R. Tarek. 1990. A novel mechanism of capillary growth in the rat pulmonary microcirculation. *Anat Rec.* 228:35–45.

Burridge, K., and M. Chrzanowska-Wodnicka. 1996. Focal adhesions, contractility, and signaling. *Annu Rev Cell Dev Biol.* 12:463–518.

Cai, W. J., S. Koltai, E. Kocsis, D. Scholz, W. Schaper, and J. Schaper. 2001. Connexin37, not Cx40 and Cx43, is induced in vascular smooth muscle cells during coronary arteriogenesis. *J Mol Cell Cardiol.* 33:957–67.

Camacho, P., and J. D. Lechleiter. 1995. Calreticulin inhibits repetitive intracellular Ca2+ waves. *Cell.* 82:765–71.

Campbell, P. G., S. K. Durham, J. D. Hayes, A. Suwanichkul, and D. R. Powell. 1999. Insulin-like growth factor-binding protein-3 binds fibrinogen and fibrin. *J Biol Chem.* 274:30215–21.

Cleaver, O., and P. A. Krieg. 1999. Molecular mechanism of vascular development. In Heart Development. R. P. Harver and N. Rosenthal, editors. Academic Press. 221–252.

Cleaver, O., K. F. Tonissen, M. S. Saha, and P. A. Krieg. 1997. Neovascularization of the Xenopus embryo. *Dev Dyn.* 210:66–77.

Coffin, J. D., and T. J. Poole. 1988. Embryonic vascular development: immunohistochemical identification of the origin and subsequent morphogenesis of the major vessel primordia in quail embryos. *Development.* 102:735–48.

Coppolino, M., C. Leung-Hagesteijn, S. Dedhar, and J. Wilkins. 1995. Inducible interaction of integrin alpha 2 beta 1 with calreticulin. Dependence on the activation state of the integrin. *J Biol Chem.* 270:23132–8.

Coppolino, M. G., M. J. Woodside, N. Demaurex, S. Grinstein, R. St-Arnaud, and S. Dedhar. 1997. Calreticulin is essential for integrin-mediated calcium signalling and cell adhesion. *Nature.* 386:843–7.

Cox, E. A., and A. Huttenlocher. 1998. Regulation of integrin-mediated adhesion during cell migration. *Microsc Res Tech.* 43:412–9.

Dai, E., M. Stewart, B. Ritchie, N. Mesaeli, S. Raha, D. Kolodziejczyk, M. L. Hobman, L. Y. Liu, W. Etches, N. Nation, M. Michalak, and A. Lucas. 1997. Calreticulin, a potential vascular regulatory protein, reduces intimal hyperplasia after arterial injury. *Arterioscler Thromb Vasc Biol.* 17:2359–68.

Daniel, J. M., and A. B. Reynolds. 1997. Tyrosine phosphorylation and cadherin/catenin function. *Bioessays.* 19:883–91.

Davis, S., T. H. Aldrich, P. F. Jones, A. Acheson, D. L. Compton, V. Jain, T. E. Ryan, J. Bruno, C. Radziejewski, P. C. Maisonpierre, and G. D. Yancopoulos. 1996. Isolation of angiopoietin-1, a ligand for the TIE2 receptor, by secretion-trap expression cloning [see comments]. *Cell.* 87:1161–9.

Dedhar, S., P. S. Rennie, M. Shago, C. Y. Hagesteijn, H. Yang, J. Filmus, R. G. Hawley, N. Bruchovsky, H. Cheng, R. J. Matusik, and et al. 1994. Inhibition of nuclear hormone receptor activity by calreticulin. *Nature.* 367: 480–3.

Delorme, B., E. Dahl, T. Jarry-Guichard, J. P. Briand, K. Willecke, D. Gros, and M. Theveniau-Ruissy. 1997. Expression pattern of connexin gene products at the early developmental stages of the mouse cardiovascular system. *Circ Res.* 81:423–37.

Drake, C. J., L. A. Davis, and C. D. Little. 1992. Antibodies to beta 1-integrins cause alterations of aortic vasculogenesis, in vivo. *Dev Dyn.* 193:83–91.

Dumont, D. J., G. H. Fong, M. C. Puri, G. Gradwohl, K. Alitalo, and M. L. Breitman. 1995. Vascularization of the mouse embryo: a study of flk-1, tek, tie, and vascular endothelial growth factor expression during development. *Dev Dyn.* 203:80–92.

Dumont, D. J., G. Gradwohl, G. H. Fong, M. C. Puri, M. Gertsenstein, A. Auerbach, and M. L. Breitman. 1994. Dominant-negative and targeted null mutations in the endothelial receptor tyrosine kinase, tek, reveal a critical role in vasculogenesis of the embryo. *Genes Dev.* 8:1897–909.

Dumont, D. J., T. P. Yamaguchi, R. A. Conlon, J. Rossant, and M. L. Breitman. 1992. tek, a novel tyrosine kinase gene located on mouse chromosome 4, is expressed in endothelial cells and their presumptive precursors. *Oncogene.* 7:1471–80.

Dvorak, H. F., L. F. Brown, M. Detmar, and A. M. Dvorak. 1995. Vascular permeability factor/vascular endothelial growth factor, microvascular hyperpermeability, and angiogenesis. *Am J Pathol.* 146:1029–39.

Ekblom, P., H. Sariola, M. Karkinen, and L. Saxen. 1982. The origin of the glomerular endothelium. *Cell Differ.* 11:35–39.

Enjolras, O., M. Wassef, E. Mazoyer, I. J. Frieden, P. N. Rieu, L. Drouet, A. Taieb, J. F. Stalder, and J. P. Escande. 1997. Infants with Kasabach-Merritt syndrome do not have "true" hemangiomas. *J Pediatr.* 130:631–40.

Fadel, M. P., E. Dziak, C. M. Lo, J. Ferrier, N. Mesaeli, M. Michalak, and M. Opas. 1999. Calreticulin affects focal contact-dependent but not close contact-dependent cell-substratum adhesion. *J Biol Chem.* 274:15085–94.

Flamme, I., and W. Risau. 1992. Induction of vasculogenesis and hematopoiesis in vitro. *Development.* 116:435–9.

Flamme, I., M. von Reutern, H. C. Drexler, S. Syed-Ali, and W. Risau. 1995. Overexpression of vascular endothelial growth factor in the avian embryo induces hypervascularization and increased vascular permeability without alterations of embryonic pattern formation. *Dev Biol.* 171:399–414.

Folkman, J., and M. Klagsbrun. 1987. Angiogenic factors. *Science.* 235:442–7.

Gampper, T. J., and R. F. Morgan. 2002. Vascular anomalies: hemangiomas. *Plast Reconstr Surg.* 110:572–85; quiz 586; discussion 587–8.

Gao, B., R. Adhikari, M. Howarth, K. Nakamura, M. C. Gold, A. B. Hill, R. Knee, M. Michalak, and T. Elliott. 2002. Assembly and antigen-presenting function of MHC class I molecules in cells lacking the ER chaperone calreticulin. *Immunity.* 16:99–109.

Gurjar, M. V., R. V. Sharma, and R. C. Bhalla. 1999. eNOS gene transfer inhibits smooth muscle cell migration and MMP-2 and MMP-9 activity. *Arterioscler Thromb Vasc Biol.* 19:2871–7.

Hammond, C., and A. Helenius. 1995. Quality control in the secretory pathway. *Curr Opin Cell Biol.* 7:523–9.

Harris, N. R., S. P. Whitt, J. Zilberberg, J. S. Alexander, and R. E. Rumbaut. 2002. Extravascular transport of fluorescently labeled albumins in the rat mesentery. *Microcirculation.* 9:177–87.

Hebert, D. N., J. X. Zhang, W. Chen, B. Foellmer, and A. Helenius. 1997. The number and location of glycans on influenza hemagglutinin determine folding and association with calnexin and calreticulin. *J Cell Biol.* 139: 613–23.

Helenius, A., E. S. Trombetta, D. N. Herbert, and J. F. Simons. 1997. Calnexin, calreticulin and the folding of glycoproteins. *Trends in Cell Biology.* 7:193–200.

Hynes, R. O. 1990. Fibronectins. Springer-Verlag, New York.

Ingber, D. E. 2002. Mechanical signaling and the cellular response to extracellular matrix in angiogenesis and cardiovascular physiology. *Circ Res.* 91:877–87.

Ishii, T., and N. Asuwa. 2000. Collagen and elastin degradation by matrix metalloproteinases and tissue inhibitors of matrix metalloproteinase in aortic dissection. *Hum Pathol.* 31:640–6.

Ito, H., Y. Seyama, and S. Kubota. 2001. Calreticulin is directly involved in anti-alpha3 integrin antibody-mediated secretion and activation of matrix metalloprotease-2. *Biochem Biophys Res Commun.* 283:297–302.

Jacob, M. P., C. Badier-Commander, V. Fontaine, Y. Benazzoug, L. Feldman, and J. B. Michel. 2001. Extracellular matrix remodeling in the vascular wall. *Pathol Biol (Paris).* 49:326–32.

Jones, E. W., and M. Orkin. 1989. Tufted angioma (angioblastoma). A benign progressive angioma, not to be confused with Kaposi's sarcoma or low-grade angiosarcoma. *J Am Acad Dermatol.* 20:214–25.

Joterau, F., and N. Le Douarin. 1978. The developmental relationship between osteocytes and osteoclasts: A study using the quail chick nuclear marker in endochondral ossification. *Dev Biol.* 63:253–265.

Klagsbrun, M., and P. A. D'Amore. 1991. Regulators of angiogenesis. *Annu Rev Physiol.* 53:217–39.

Le Lievre, C. S., and N. M. Le Douarin. 1975. Mesenchymal derevatives of neural crest. Analysis of chimeric quail and chick embryos. *J Embryol Exp Morphol.* 34:125–154.

Leung-Hagesteijn, C. Y., K. Milankov, M. Michalak, J. Wilkins, and S. Dedhar. 1994. Cell attachment to extracellular matrix substrates is inhibited upon downregulation of expression of calreticulin, an intracellular integrin alpha-subunit-binding protein. *J Cell Sci.* 107:589–600.

Li, L., J. M. Miano, B. Mercer, and E. N. Olson. 1996. Expression of the SM22alpha promoter in transgenic mice provides evidence for distinct transcriptional regulatory programs in vascular and visceral smooth muscle cells. *J Cell Biol.* 132:849–59.

Lin, S. K., C. P. Chiang, C. Y. Hong, C. P. Lin, W. H. Lan, C. C. Hsieh, and M. Y. Kuo. 1997. Immunolocalization of interstitial collagenase (MMP-1) and tissue inhibitor of metalloproteinases-1 (TIMP-1) in radicular cysts. *J Oral Pathol Med.* 26:458–63.

Little, T. L., J. Xia, and B. R. Duling. 1995. Dye tracers define differential endothelial and smooth muscle coupling patterns within the arteriolar wall. *Circ Res.* 76:498–504.

Liu, N., R. E. Fine, E. Simons, and R. J. Johnson. 1994. Decreasing calreticulin expression lowers the Ca2+ response to bradykinin and increases sensitivity to ionomycin in NG-108-15 cells. *J Biol Chem.* 269:28635–9.

Manasek, F. J. 1971. The ultrastructure of embryonic myocardial blood vessels. *Dev Biol.* 26:42–54.

McDonnell, J. M., G. E. Jones, T. K. White, and M. L. Tanzer. 1996. Calreticulin binding affinity for glycosylated laminin. *J Biol Chem.* 271:7891–4.

Mentzel, T., A. Beham, E. Calonje, D. Katenkamp, and C. D. Fletcher. 1997. Epithelioid hemangioendothelioma of skin and soft tissues: clinicopathologic and immunohistochemical study of 30 cases. *Am J Surg Pathol.* 21:363–74.

Mery, L., N. Mesaeli, M. Michalak, M. Opas, D. P. Lew, and K. H. Krause. 1996. Overexpression of calreticulin increases intracellular Ca2+ storage and decreases store-operated Ca2+ influx. *J Biol Chem.* 271:9332–9.

Mesaeli, N., I. Ahsan, R. Knee, M. Dabrowska, J. J. M. Bergeron, D. Y. Thomas, M. Opas, and M. Michalak. 2000. Endoplasmic reticulum chaperones in calreticulin deficient mouse embryonic fibroblast cells. *Molecular Biology of the cell.* 11:491a.

Mesaeli, N., and M. Michalak. 1995. Calreticulin is a major Ca binding protein of the rat aortic smooth muscle cells. In Pathophysiology of Heart Failure. N. S. ZDhalla, S. P. K., N. Takeda, and R. E. Beamish, editors. Kluwer Academic Publisher, Boston. 245–251.

Mesaeli, N., K. Nakamura, E. Zvaritch, P. Dickie, E. Dziak, K. H. Krause, M. Opas, D. H. MacLennan, and M. Michalak. 1999. Calreticulin is essential for cardiac development. *J Cell Biol.* 144:857–68.

Michalak, M. 1996. Calreticulin. R. G. Landes Company, Austin, Tex. 211 pp.

Michalak, M., K. Burns, C. Andrin, N. Mesaeli, G. H. Jass, J. L. Busaan, and M. Opas. 1996. Endoplasmic reticulum form of calreticulin modulates glucocorticoid-sensitive gene expression. *J Biol Chem.* 271:29436–45.

Michalak, M., K. P. Campbell, and D. H. MacLennan. 1980. Localization of the high affinity calcium binding protein and an intrinsic glycoprotein in sarcoplasmic reticulum membranes. *J Biol Chem.* 255:1317–26.

Michalak, M., E. F. Corbett, N. Mesaeli, K. Nakamura, and M. Opas. 1999. Calreticulin: one protein, one gene, many functions [In Process Citation]. *Biochem J.* 344 Pt 2:281–92.

Michalak, M., R. E. Milner, K. Burns, and M. Opas. 1992. Calreticulin. *Biochem J.* 285:681–92.

Milner, R. E., S. Baksh, C. Shemanko, M. R. Carpenter, L. Smillie, J. E. Vance, M. Opas, and M. Michalak. 1991. Calreticulin, and not calsequestrin, is the major calcium binding protein of smooth muscle sarcoplasmic reticulum and liver endoplasmic reticulum. *J Biol Chem.* 266:7155–65.

Milner, R. E., K. S. Famulski, and M. Michalak. 1992. Calcium binding proteins in the sarcoplasmic/endoplasmic reticulum of muscle and nonmuscle cells. *Mol Cell Biochem.* 112:1–13.

Nakamura, K., M. Robertson, G. Liu, P. Dickie, J. Q. Guo, H. J. Duff, M. Opas, K. Kavanagh, and M. Michalak. 2001a. Complete heart block and sudden death in mice overexpressing calreticulin. *J Clin Invest.* 107:1245–53.

Nakamura, K., A. Zuppini, S. Arnaudeau, J. Lynch, I. Ahsan, R. Krause, S. Papp, H. De Smedt, J. B. Parys, W. Muller-Esterl, D. P. Lew, K. H. Krause, N. Demaurex, M. Opas, and M. Michalak. 2001b. Functional specialization of calreticulin domains. *J Cell Biol.* 154:961–72.

Nauseef, W. M., S. J. McCormick, and R. A. Clark. 1995. Calreticulin functions as a molecular chaperone in the biosynthesis of myeloperoxidase. *J Biol Chem.* 270:4741–7.

Nigam, S. K., A. L. Goldberg, S. Ho, M. F. Rohde, K. T. Bush, and M. Sherman. 1994. A set of endoplasmic reticulum proteins possessing properties of molecular chaperones includes Ca(2+)-binding proteins and members of the thioredoxin superfamily. *J Biol Chem.* 269:1744–9.

Noden, D. M. 1988. Interactions and fates of avian craniofacial mesenchyme. *Development.* 103:121–40.

Opas, M., M. Szewczenko-Pawlikowski, G. K. Jass, N. Mesaeli, and M. Michalak. 1996. Calreticulin modulates cell adhesiveness via regulation of vinculin expression. *J Cell Biol.* 135:1913–23.

Ostwald, T. J., D. H. MacLennan, and K. J. Dorrington. 1974. Effects of cation binding on the conformation of calsequestrin and the high affinity calcium-binding protein of sarcoplasmic reticulum. *J Biol Chem.* 249:5867–71.

Pardanaud, L., F. Yassine, and F. Dieterlen-Lievre. 1989. Relationship between vasculogenesis, angiogenesis and haemopoiesis during avian ontogeny. *Development.* 105:473–85.

Patan, S., B. Haenni, and P. H. Burri. 1993. Evidence for intussusceptive capillary growth in the chicken chorioallantoic membrane (CAM). *Anat Embryol* (Berl). 187:121–30.

Patan, S., B. Haenni, and P. H. Burri. 1996. Implementation of intussusceptive microvascular growth in the chicken chorioallantoic membrane (CAM): 1. pillar formation by folding of the capillary wall. *Microvasc Res.* 51:80–98.

Paziuk, T., and N. Mesaeli. 2002. Impaired Ca release by P2Y receptor in calreticulin null cells is due to altered IP3 receptor expression. *Journal of Molecular Cellular Cardiology.* 34:A19–01.

Peracchia, F., A. Tamburro, C. Prontera, B. Mariani, and D. Rotilio. 1997. cAMP involvement in the expression of MMP-2 and MT-MMP1 metalloproteinases in human endothelial cells. *Arterioscler Thromb Vasc Biol.* 17:3185–90.

Perkins, P., and S. W. Weiss. 1996. Spindle cell hemangioendothelioma. An analysis of 78 cases with reassessment of its pathogenesis and biologic behavior. *Am J Surg Pathol.* 20:1196–204.

Peters, K. G., C. De Vries, and L. T. Williams. 1993. Vascular endothelial growth factor receptor expression during embryogenesis and tissue repair suggests a role in endothelial differentiation and blood vessel growth. *Proc Natl Acad Sci U S A.* 90:8915–9.

Peterson, J. R., A. Ora, P. N. Van, and A. Helenius. 1995. Transient, lectin-like association of calreticulin with folding intermediates of cellular and viral glycoproteins. *Mol Biol Cell.* 6:1173–84.

Pike, S. E., L. Yao, J. Setsuda, K. D. Jones, B. Cherney, E. Appella, K. Sakaguchi, H. Nakhasi, C. D. Atreya, J. Teruya-Feldstein, P. Wirth, G. Gupta, and G. Tosato. 1999. Calreticulin and calreticulin fragments are endothelial cell inhibitors that suppress tumor growth. *Blood.* 94:2461–8.

Poole, T. J., and J. D. Coffin. 1989. Vasculogenesis and angiogenesis: two distinct morphogenetic mechanisms establish embryonic vascular pattern. *J Exp Zool.* 251:224–31.

Powell, J. 1999. Update on hemangiomas and vascular malformations. *Curr Opin Pediatr.* 11:457–63.

Pozzan, T., R. Rizzuto, P. Volpe, and J. Meldolesi. 1994. Molecular and cellular physiology of intracellular calcium stores. *Physiol Rev.* 74:595–636.

Reidy, M. A., and S. M. Schwartz. 1981. Endothelial regeneration. Ill. Time course of intimal changes after small defined injury to rat aortic endothelium. *Lab Invest.* 44:301–8.

Risau, W., and 1. Flamme. 1995. Vasculogenesis. *Annu Rev Cell Dev Biol.* 11:73–91.

Risau, W., and V. Lemmon. 1988. Changes in the vascular extracellular matrix during embryonic vasculogenesis and angiogenesis. *Development* (Cambridge). 102:471–478.

Rojiani, M. V., B. B. Finlay, V. Gray, and S. Dedhar. 1991. In vitro interaction of a polypeptide homologous to human Ro/SS-A antigen (calreticulin) with a highly conserved amino acid sequence in the cytoplasmic domain of integrin alpha subunits. *Biochemistry.* 30:9859–66.

Rosenbloom, J., W. R. Abrams, and R. Mecham. 1993. Extracellular matrix 4: the elastic fiber. *Faseb J.* 7:1208–18.

Sato, T. N., Y. Tozawa, U. Deutsch, K. Wolburg-Buchholz, Y. Fujiwara, M. Gendron-Maguire, T. Gridley, H. Wolburg, W. Risau, and Y. Qin. 1995. Distinct roles of the receptor tyrosine kinases Tie-1 and Tie-2 in blood vessel formation. *Nature.* 376:70–4.

Seeger, F. H., E. Blessing, L. Gu, R. Bornhold, S. Denger, and J. Kreuzer. 2002. Fibrinogen induces chemotactic activity in endothelial cells. *Acta Physiol Scand.* 176:109–15.

Sheu, J. R., M. H. Yen, Y. C. Kan, W. C. Hung, P. T. Chang, and H. N. Luk. 1997. Inhibition of angiogenesis in vitro and in vivo: comparison of the relative activities of triflavin, an Arg-Gly-Asp-containing peptide and anti-alpha(v)beta3 integrin monoclonal antibody. *Biochim Biophys Acta.* 1336:445–54.

Simon, A. M., and A. R. McWhorter. 2002. Vascular abnormalities in mice lacking the endothelial gap junction proteins connexin37 and connexin40. *Dev Biol.* 251:206–20.

Spiro, R. G., Q. Zhu, V. Bhoyroo, and H. D. Soling. 1996. Definition of the lectin-like properties of the molecular chaperone, calreticulin, and demonstration of its copurification with endomannosidase from rat liver Golgi. *J Biol Chem.* 271:11588–94.

Stewart, P. A., and M. J. Wiley. 1981. Developing nervous tissue induces formation of blood-brain barrier characteristics in invading endothelial cells: a study using quail—chick transplantation chimeras. *Dev Biol.* 84:183–92.

Suri, C., P. F. Jones, S. Patan, S. Bartunkova, P. C. Maisonpierre, S. Davis, T. N. Sato, and G. D. Yancopoulos. 1996. Requisite role of angiopoietin-1, a ligand for the TIE2 receptor, during embryonic angiogenesis [see comments]. *Cell.* 87:1171–80.

Tezono, K., K. P. Sarker, H. Kikuchi, M. Nasu, I. Kitajima, and 1. Maruyama. 2001. Bioactivity of the vascular endothelial growth factor trapped in fibrin clots: production of IL-6 and IL-8 in monocytes by fibrin clots. *Haemostasis.* 31:71–9.

Tharin, S., E. Dziak, M. Michalak, and M. Opas. 1992. Widespread tissue distribution of rabbit calreticulin, a non-muscle functional analogue of calsequestrin. *Cell Tissue Res.* 269:29–37.

Tirasophon, W., A. A. Welihinda, and R. J. Kaufman. 1998. A stress response pathway from the endoplasmic reticulum to the nucleus requires a novel bifunctional protein kinase/endoribonuclease (Ire1p) in mammalian cells. *Genes Dev.* 12:1812–24.

Traverse, J. H., J. R. Lesser, B. P. Flygenring, T. H. Bracken, O. M. Olevsky, D. M. Nicoloff, T. Flavin, C. A. Horwitz, and R. G. Hauser. 1999. Epithelioid hemangioendothelioma of the thoracic aorta resulting in aortic obstruction and congestive heart failure. *Circulation.* 100:564–5.

Trussard, A. A., Mawji, N. M., Ong, C., Mui, A., St.-Arnaud, R., Dedhar, S. 2003. Conditional knock-out of integrin linked kinase demonstrates an essential role in protein kinase B/Akt activation. *J. Biol. Chem.* 278:22374–22378.

Underwood, P. A., P. A. Bean, and J. M. Whitelock. 1998. Inhibition of endothelial cell adhesion and proliferation by extracellular matrix from vascular smooth muscle cells: role of type V collagen. *Atherosclerosis.* 141:141–52.

van der Rest, M., and R. Garrone. 1991. Collagen family of proteins. *Faseb J.* 5:2814–23.

van Groningen, J. P., A. C. Wenink, and L. H. Testers. 1991. Myocardial capillaries: increase in number by splitting of existing vessels. *Anat Embryol.* 184:65–70.

van Kempen, M. J., and H. J. Jongsma. 1999. Distribution of connexin37, connexin40 and connexin43 in the aorta and coronary artery of several mammals. *Histochem Cell Biol.* 112:479–86.

Welihinda, A. A., W. Tirasophon, S. R. Green, and R. J. Kaufman. 1997. Gene induction in response to unfolded protein in the endoplasmic reticulum is mediated through Ire1p kinase interaction with a transcriptional coactivator complex containing Ada5p. *Proc Natl Acad Sci U S A.* 94:4289–94.

Wheeler, D. G., J. Horsford, M. Michalak, J. H. White, and G. N. Hendy. 1995. Calreticulin inhibits vitamin D3 signal transduction. *Nucleic Acids Res.* 23:3268–74.

Wigle, J. T., K. Chowdhury, P. Gruss, and G. Oliver. 1999. Prox1 function is crucial for mouse lens-fibre elongation. *Nat Genet.* 21:318–22.

Winrow, C. J., K. S. Miyata, S. L. Marcus, K. Burns, M. Michalak, J. P. Capone, and R. A. Rachubinski. 1995. Calreticulin modulates the in vitro DNA binding but not the in vivo transcriptional activation by peroxisome proliferator-activated receptor/retinoid X receptor heterodimers. *Mol Cell Endocrinol.* 111:175–9.

Xia, J., T. L. Little, and B. R. Duling. 1995. Cellular pathways of the conducted electrical response in arterioles of hamster cheek pouch in vitro. *Am J Physiol.* 269:H2031–8.

Yang, J. T., H. Rayburn, and R. O. Hynes. 1993. Embryonic mesodermal defects in alpha 5 integrin-deficient mice. *Development.* 119:1093–105.

The invention claimed is:

1. A transgenic mouse whose genome comprises
a transgene comprising mouse SM22α promoter operably linked to a cDNA encoding the calreticulin (CRT) peptide as set forth in SEQ ID No. 23,
wherein expression of calreticulin from the mouse SM22α promoter in the vascular smooth muscle cells of the transgenic mouse results in hemangioma formation.

2. A transgene comprising mouse SM22α promoter operably linked to a cDNA encoding the calreticulin peptide as set forth in SEQ ID No. 23.

3. A method for producing a transgenic mouse that exhibits hemangioma comprising:

introducing into a fertilized mouse egg a transgene comprising mouse SM22α promoter operably linked to a cDNA encoding the calreticulin (CRT) peptide, as set forth in SEQ ID NO. 23,
transplanting the injected egg in a foster parent female mouse; and
selecting a mouse derived from an injected egg whose genome comprises mouse SM22α promoter operably linked to a cDNA encoding the calreticulin peptide as set forth in SEQ ID No. 23,
wherein expression of calreticulin from the mouse SM22α promoter in the vascular smooth muscle cells of the transgenic mouse results in hemangioma formation.

4. The transgenic mouse according to claim 1 wherein the mouse SM22α promoter is the DNA sequence corresponding to nucleotides 1 to 1343 of SEQ ID No. 1.

5. The method according to claim 3 wherein the mouse SM22α promoter is nucleotides 1 to 1343 of SEQ ID No. 1.

6. The transgene according to claim 2 wherein the transgene is nucleotides 1 to 2655 of SEQ ID No. 1.

7. The transgene according to claim 2 wherein the transgene is nucleotides 1 to 2691 of SEQ ID No. 12.

* * * * *

SEQUENCE LISTING

<160> NUMBER OF SEQ ID NOS: 24

<210> SEQ ID NO 1
<211> LENGTH: 2655
<212> TYPE: DNA
<213> ORGANISM: Artificial
<220> FEATURE:
<223> OTHER INFORMATION: artificial construct of sm22a promoter and CRT cDNA
<220> FEATURE:
<221> NAME/KEY: CDS
<222> LOCATION: (1319)..(2653)
<223> OTHER INFORMATION: CRT coding sequence

<400> SEQUENCE: 1

```
cccttcctt cagatgccac aaggaggtgc tggagttcta tgcaccaata gcttaaacca      60
gccaggctgg ctgtagtgga ttgagcgtct gaggctgcac ctctctggcc tgcagccagt     120
tcctgggtga gactgaccct gcctgagggt tctctccttc cctctctcta ctcctttcct    180
ccctctccct ctccctctct ctgtttcctg aggtttccag gattggggat gggactcaga    240
gacaccacta aagccttacc ttttaagaag ttgcattcag tgagtgtgtg agacatagca    300 cagataggg cagaggagag ctggttctgt ctccactgtg tttggtcttg ggtactgaac     360
tcagaccatc aggtgtgata gcagttgtct ttaaccctaa ccctgagcct gtctcacctg    420
tcccttccca agaccactga agctaggtgc aagataagtg gggaccctt ctgaggtggt    480 aggatctttc acgataagga ctattttgaa gggaggggagg gtgacactgt cctagtcctc   540
ttaccctagt gtcctccagc cttgccaggc cttaaacatc cgcccattgt caccgctcta   600
gaaggggcca gggttgactt gctgctaaac aaggcactcc ctagagaagc acccgctaga   660
agcataccat acctgtgggc aggatgaccc atgttctgcc acgcacttgg tagccttgga    720
aaggccactt tgaacctcaa ttttctcaac tgttaaatgg ggtggtaact gctatctcat    780
aataaggggg aacgtgaaag gaaggcgttt gcatagtgcc tggttgtgca gccaggctgc    840
agtcaagact agttcccacc aactcgattt taaagcttg caagaaggtg gcttgtttgt     900
cccttgcagg ttcctttgtc gggccaaact ctagaatgcc tccccctttc tttctcattg    960
aagagcagac ccaagtccgg gtaacaagga agggtttcag ggtcctgccc ataaaaggtt   1020 tttccggcc gccctcagca ccgccccgcc ccgaccccg cagcatctcc aaagcatgca     1080
gagaatgtct ccggctgccc ccgacagact gctccaactt ggtgtctttc cccaaatatg   1140
gagcctgtgt ggagtgagtg gggcggcccg gggtggtgag ccaagcagac ttccatgggc   1200
agggaggggc gccagcggac ggcagagggg tgacatcact gcctaggcgg cctttaaacc   1260
cctcacccag ccggcgcccc accgagctcg gatccactag tccagtgtgg tggaattc    1318
```

```
atg ctg ctc cct gtg ccg ctg ctg ctc ggc ctg ctc ggc ctg gcc gcc    1366
Met Leu Leu Pro Val Pro Leu Leu Leu Gly Leu Leu Gly Leu Ala Ala
1               5                   10                  15 gcc gag ccc gtc gtc tac ttc aag gag cag ttt ctg gac gga gat ggg    1414
Ala Glu Pro Val Val Tyr Phe Lys Glu Gln Phe Leu Asp Gly Asp Gly
            20                  25                  30 tgg acc gag cgc tgg atc gaa tcc aaa cac aag tcc gat ttt ggc aaa    1462
Trp Thr Glu Arg Trp Ile Glu Ser Lys His Lys Ser Asp Phe Gly Lys
        35                  40                  45 ttc gtc ctc agt tcg ggc aag ttc tac ggc gat cag gag aaa gat aaa    1510
Phe Val Leu Ser Ser Gly Lys Phe Tyr Gly Asp Gln Glu Lys Asp Lys
    50                  55                  60
```

-continued

| | | |
|---|---|---|
| ggg ctg cag acc agc cag gac gcc cgc ttc tac gcc ctg tcg gcc cga<br>Gly Leu Gln Thr Ser Gln Asp Ala Arg Phe Tyr Ala Leu Ser Ala Arg<br>65                        70                        75                        80 | 1558 |
| ttc gag ccg ttc agc aac aag ggc cag cca ctg gtg gtg cag cca gcc<br>Phe Glu Pro Phe Ser Asn Lys Gly Gln Pro Leu Val Val Gln Pro Ala<br>                        85                        90                        95 | 1606 |
| agg acg ccc gct tct acg ccc tgt cgg ccc gat cgc agc cgt tca gca<br>Arg Thr Pro Ala Ser Thr Pro Cys Arg Pro Asp Ser Ser Arg Ser Ala<br>                 100                     105                     110 | 1654 |
| aca agg gcc agc cac tgg tgg tgc agt tca ccg tga aac acg agc aga<br>Thr Arg Ala Ser His Trp Trp Cys Ser Ser Pro     Asn Thr Ser Arg<br>               115                     120                        125 | 1702 |
| aca ttg act gcg ggg gcg gct acg tga agc tgt ttc cgg ccg gcc tgg<br>Thr Leu Thr Ala Gly Ala Ala Thr     Ser Cys Phe Arg Pro Ala Trp<br>               130                     135                         140 | 1750 |
| acc aga agg aca tgc acg ggg act ctg agt aca aca tca tgt ttg gtc<br>Thr Arg Arg Thr Cys Thr Gly Thr Leu Ser Thr Thr Ser Cys Leu Val<br>               145                     150                     155 | 1798 |
| ctg aca tct gtg gcc ccg gca cca aga agg ttc acg tca tct tca act<br>Leu Thr Ser Val Ala Pro Ala Pro Arg Arg Phe Thr Ser Ser Ser Thr<br>     160                     165                     170 | 1846 |
| aca agg gca aga acg tgc tga tca aca agg aca tcc gtt gca agg acg<br>Thr Arg Ala Arg Thr Cys     Ser Thr Arg Thr Ser Val Ala Arg Thr<br>175                     180                         185 | 1894 |
| acg agt tca cac acc tgt aca cgc tga tcg tgc ggc cgg aca aca cgt<br>Thr Ser Ser His Thr Cys Thr Arg     Ser Cys Gly Arg Thr Thr Arg<br>190                     195                         200 | 1942 |
| atg agg tga aga ttg aca aca gcc agg tgg agt cgg gct ccc tgg agg<br>Met Arg     Arg Leu Thr Thr Ala Arg Trp Ser Arg Ala Pro Trp Arg<br>205                          210                       215 | 1990 |
| atg act ggg act tcc tac ccc cca aga aga taa agg acc cag atg cct<br>Met Thr Gly Thr Ser Tyr Pro Pro Arg Arg     Arg Thr Gln Met Pro<br>220                         225                         230 | 2038 |
| cga agc ctg aag act ggg acg agc ggg cca aga tcg acg acc cca cgg<br>Arg Ser Leu Lys Thr Gly Thr Ser Gly Pro Arg Ser Thr Thr Pro Arg<br>235                     240                     245                     250 | 2086 |
| act cca agc ccg agg act ggg aca agc ccg agc aca tcc ccg acc cgg<br>Thr Pro Ser Pro Arg Thr Gly Thr Ser Pro Ser Thr Ser Pro Thr Arg<br>                        255                     260                     265 | 2134 |
| acg cga aga agc ccg aag act ggg acg aag aaa tgg acg gag agt ggg<br>Thr Arg Arg Ser Pro Lys Thr Gly Thr Lys Lys Trp Thr Glu Ser Gly<br>               270                     275                     280 | 2182 |
| agc cgc cgg tga ttc aga acc ccg agt aca agg gtg agt gga agc cgc<br>Ser Arg Arg     Phe Arg Thr Pro Ser Thr Arg Val Ser Gly Ser Arg<br>     285                     290                     295 | 2230 |
| ggc aga tcg aca acc ccg att aca aag gca cct gga tcc acc ccg aaa<br>Gly Arg Ser Thr Thr Pro Ile Thr Lys Ala Pro Gly Ser Thr Pro Lys<br>          300                     305                     310 | 2278 |
| tcg aca acc ccg agt act cgc ccg acg cta aca tct atg cct acg aca<br>Ser Thr Thr Pro Ser Thr Arg Pro Thr Leu Thr Ser Met Pro Thr Thr<br>     315                     320                     325 | 2326 |
| gct ttg ccg tgc tgg gct tgg acc tct ggc agg tca agt cgg gca cca<br>Ala Leu Pro Cys Trp Ala Trp Thr Ser Gly Arg Ser Ser Arg Ala Pro<br>330                     335                     340                     345 | 2374 |
| tct tcg aca act tcc tca tca cca acg atg agg cgt acg cag agg agt<br>Ser Ser Thr Thr Ser Ser Ser Pro Thr Met Arg Arg Thr Gln Arg Ser<br>                        350                     355                     360 | 2422 |
| ttg gca acg aga cgt ggg gcg tca cca aga cgg ccg aga agc aga tga<br>Leu Ala Thr Arg Arg Gly Ala Ser Pro Arg Arg Pro Arg Ser Arg<br>                        365                     370                     375 | 2470 |

```
aag aca agc agg acg agg agc agc gga tga agg agg agg agg aga        2518
Lys Thr Ser Arg Thr Arg Ser Ser Gly     Arg Arg Arg Arg Arg
        380                 385                 390 aga agc gga agg agg agg agg ccg agg agg acg agg agg aca agg        2566
Arg Ser Gly Arg Arg Arg Arg Pro Arg Arg Thr Arg Arg Thr Arg
            395                 400                 405 acg aca agg agg acg agg atg agg acg agg agg aca agg acg agg agg    2614
Thr Thr Arg Arg Thr Arg Met Arg Thr Arg Arg Thr Arg Thr Arg Arg
        410                 415                 420 agg agg agg cgg ccg ccg gcc agg cca agg acg agc tgt ag             2655
Arg Arg Arg Arg Pro Pro Ala Arg Pro Arg Thr Ser Cys
    425                 430                 435

<210> SEQ ID NO 2
<211> LENGTH: 123
<212> TYPE: PRT
<213> ORGANISM: Artificial
<220> FEATURE:
<223> OTHER INFORMATION: Synthetic Construct

<400> SEQUENCE: 2

Met Leu Leu Pro Val Pro Leu Leu Gly Leu Leu Gly Leu Ala Ala
1               5                   10                  15

Ala Glu Pro Val Val Tyr Phe Lys Glu Gln Phe Leu Asp Gly Asp
                20                  25                  30

Trp Thr Glu Arg Trp Ile Glu Ser Lys His Lys Ser Asp Phe Gly Lys
            35                  40                  45

Phe Val Leu Ser Ser Gly Lys Phe Tyr Gly Asp Gln Glu Lys Asp Lys
    50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Pro Ala
                85                  90                  95

Arg Thr Pro Ala Ser Thr Pro Cys Arg Pro Asp Ser Ser Arg Ser Ala
                100                 105                 110

Thr Arg Ala Ser His Trp Trp Cys Ser Ser Pro
            115                 120

<210> SEQ ID NO 3
<211> LENGTH: 12
<212> TYPE: PRT
<213> ORGANISM: Artificial
<220> FEATURE:
<223> OTHER INFORMATION: Synthetic Construct

<400> SEQUENCE: 3

Asn Thr Ser Arg Thr Leu Thr Ala Gly Ala Ala Thr
1               5                   10

<210> SEQ ID NO 4
<211> LENGTH: 45
<212> TYPE: PRT
<213> ORGANISM: Artificial
<220> FEATURE:
<223> OTHER INFORMATION: Synthetic Construct

<400> SEQUENCE: 4

Ser Cys Phe Arg Pro Ala Trp Thr Arg Arg Thr Cys Thr Gly Thr Leu
1               5                   10                  15

Ser Thr Thr Ser Cys Leu Val Leu Thr Ser Val Ala Pro Ala Pro Arg
                20                  25                  30
```

Arg Phe Thr Ser Ser Thr Thr Arg Ala Arg Thr Cys
            35                  40                  45

<210> SEQ ID NO 5
<211> LENGTH: 17
<212> TYPE: PRT
<213> ORGANISM: Artificial
<220> FEATURE:
<223> OTHER INFORMATION: Synthetic Construct

<400> SEQUENCE: 5

Ser Thr Arg Thr Ser Val Ala Arg Thr Thr Ser Ser His Thr Cys Thr
1               5                   10                  15

Arg

<210> SEQ ID NO 6
<211> LENGTH: 9
<212> TYPE: PRT
<213> ORGANISM: Artificial
<220> FEATURE:
<223> OTHER INFORMATION: Synthetic Construct

<400> SEQUENCE: 6

Ser Cys Gly Arg Thr Thr Arg Met Arg
1               5

<210> SEQ ID NO 7
<211> LENGTH: 23
<212> TYPE: PRT
<213> ORGANISM: Artificial
<220> FEATURE:
<223> OTHER INFORMATION: Synthetic Construct

<400> SEQUENCE: 7

Arg Leu Thr Thr Ala Arg Trp Ser Arg Ala Pro Trp Arg Met Thr Gly
1               5                   10                  15

Thr Ser Tyr Pro Pro Arg Arg
            20

<210> SEQ ID NO 8
<211> LENGTH: 56
<212> TYPE: PRT
<213> ORGANISM: Artificial
<220> FEATURE:
<223> OTHER INFORMATION: Synthetic Construct

<400> SEQUENCE: 8

Arg Thr Gln Met Pro Arg Ser Leu Lys Thr Gly Thr Ser Gly Pro Arg
1               5                   10                  15

Ser Thr Thr Pro Arg Thr Pro Ser Pro Arg Thr Gly Thr Ser Pro Ser
            20                  25                  30

Thr Ser Pro Thr Arg Thr Arg Arg Ser Pro Lys Thr Gly Thr Lys Lys
        35                  40                  45

Trp Thr Glu Ser Gly Ser Arg Arg
    50                  55

<210> SEQ ID NO 9
<211> LENGTH: 91
<212> TYPE: PRT
<213> ORGANISM: Artificial
<220> FEATURE:
<223> OTHER INFORMATION: Synthetic Construct

<400> SEQUENCE: 9

-continued

Phe Arg Thr Pro Ser Thr Arg Val Ser Gly Ser Arg Gly Arg Ser Thr
1               5                   10                  15

Thr Pro Ile Thr Lys Ala Pro Gly Ser Thr Pro Lys Ser Thr Thr Pro
            20                  25                  30

Ser Thr Arg Pro Thr Leu Thr Ser Met Pro Thr Thr Ala Leu Pro Cys
        35                  40                  45

Trp Ala Trp Thr Ser Gly Arg Ser Ser Arg Ala Pro Ser Ser Thr Thr
    50                  55                  60

Ser Ser Ser Pro Thr Met Arg Arg Thr Gln Arg Ser Leu Ala Thr Arg
65                  70                  75                  80

Arg Gly Ala Ser Pro Arg Arg Pro Arg Ser Arg
                85                  90

<210> SEQ ID NO 10
<211> LENGTH: 9
<212> TYPE: PRT
<213> ORGANISM: Artificial
<220> FEATURE:
<223> OTHER INFORMATION: Synthetic Construct

<400> SEQUENCE: 10

Lys Thr Ser Arg Thr Arg Ser Ser Gly
1               5

<210> SEQ ID NO 11
<211> LENGTH: 51
<212> TYPE: PRT
<213> ORGANISM: Artificial
<220> FEATURE:
<223> OTHER INFORMATION: Synthetic Construct

<400> SEQUENCE: 11

Arg Arg Arg Arg Arg Arg Ser Gly Arg Arg Arg Arg Pro Arg
1               5                   10                  15

Arg Thr Arg Arg Thr Arg Thr Thr Arg Arg Thr Arg Met Arg Thr Arg
            20                  25                  30

Arg Thr Arg Thr Arg Arg Arg Arg Arg Pro Pro Ala Arg Pro Arg
        35                  40                  45

Thr Ser Cys
    50

<210> SEQ ID NO 12
<211> LENGTH: 2691
<212> TYPE: DNA
<213> ORGANISM: Artificial
<220> FEATURE:
<223> OTHER INFORMATION: construct of SM22a promoter and CRT cDNA with
      HA tag inserted into CRT cDNA
<220> FEATURE:
<221> NAME/KEY: CDS
<222> LOCATION: (1319)..(2689)
<220> FEATURE:
<221> NAME/KEY: misc_feature
<222> LOCATION: (2635)..(2670)
<223> OTHER INFORMATION: HA insertion

<400> SEQUENCE: 12 cccttcctt  cagatgccac  aaggaggtgc  tggagttcta  tgcaccaata  gcttaaacca      60
gccaggctgg  ctgtagtgga  ttgagcgtct  gaggctgcac  ctctctggcc  tgcagccagt     120
tcctgggtga  gactgaccct  gcctgagggt  tctctcctcc  cctctctcta  ctcctttcct     180
ccctctccct  ctccctctct  ctgtttcctg  aggtttccag  gattggggat  gggactcaga     240

```
gacaccacta aagccttacc tttaagaag ttgcattcag tgagtgtgtg agacatagca    300
cagatagggg cagaggagag ctggttctgt ctccactgtg tttggtcttg ggtactgaac    360
tcagaccatc aggtgtgata gcagttgtct ttaaccctaa ccctgagcct gtctcacctg    420
tcccttccca agaccactga agctaggtgc aagataagtg gggaccctt ctgaggtggt     480 aggatctttc acgataagga ctattttgaa gggagggagg gtgacactgt cctagtcctc    540
ttaccctagt gtcctccagc cttgccaggc cttaaacatc cgcccattgt caccgctcta    600
gaaggggcca gggttgactt gctgctaaac aaggcactcc ctagagaagc acccgctaga    660
agcataccat acctgtgggc aggatgaccc atgttctgcc acgcacttgg tagccttgga    720
aaggccactt tgaacctcaa ttttctcaac tgttaaatgg ggtggtaact gctatctcat    780 aataagggg aacgtgaaag aaggcgtttt gcatagtgcc tggttgtgca gccaggctgc     840
agtcaagact agttcccacc aactcgattt taaagccttg caagaaggtg gcttgtttgt    900
cccttgcagg ttcctttgtc gggccaaact ctagaatgcc tcccccttc tttctcattg     960 aagagcagac ccaagtccgg gtaacaagga agggtttcag ggtcctgccc ataaaaggtt    1020
tttcccggcc gccctcagca ccgccccgcc ccgaccccg cagcatctcc aaagcatgca     1080
gagaatgtct ccggctgccc ccgacagact gctccaactt ggtgtctttc cccaaatatg    1140
gagcctgtgt ggagtgagtg gggcggcccg gggtggtgag ccaagcagac ttccatgggc    1200
agggaggggc gccagcggac ggcagagggg tgacatcact gcctaggcgg cctttaaacc    1260
cctcacccag ccggcgcccc accgagctcg gatccactag tccagtgtgg tggaattc     1318 atg ctg ctc cct gtg ccg ctg ctg ctc ggc ctg ctc ggc ctg gcc gcc    1366
Met Leu Leu Pro Val Pro Leu Leu Leu Gly Leu Leu Gly Leu Ala Ala
1               5                   10                  15 gcc gag ccc gtc gtc tac ttc aag gag cag ttt ctg gac gga gat ggg    1414
Ala Glu Pro Val Val Tyr Phe Lys Glu Gln Phe Leu Asp Gly Asp Gly
            20                  25                  30 tgg acc gag cgc tgg atc gaa tcc aaa cac aag tcc gat ttt ggc aaa    1462
Trp Thr Glu Arg Trp Ile Glu Ser Lys His Lys Ser Asp Phe Gly Lys
        35                  40                  45 ttc gtc ctc agt tcg ggc aag ttc tac ggc gat cag gag aaa gat aaa    1510
Phe Val Leu Ser Ser Gly Lys Phe Tyr Gly Asp Gln Glu Lys Asp Lys
    50                  55                  60 ggg ctg cag acc agc cag gac gcc cgc ttc tac gcc ctg tcg gcc cga    1558
Gly Leu Gln Thr Ser Gln Asp Ala Arg Phe Tyr Ala Leu Ser Ala Arg
65                  70                  75                  80 ttc gag ccg ttc agc aac aag ggc cag cca ctg gtg gtg cag cca gcc    1606
Phe Glu Pro Phe Ser Asn Lys Gly Gln Pro Leu Val Val Gln Pro Ala
                85                  90                  95 agg acg ccc gct tct acg ccc tgt cgg ccc gat tcg agc cgt tca gca    1654
Arg Thr Pro Ala Ser Thr Pro Cys Arg Pro Asp Ser Ser Arg Ser Ala
            100                 105                 110 aca agg gcc agc cac tgg tgg tgc agt tca ccg tga aac acg agc aga    1702
Thr Arg Ala Ser His Trp Trp Cys Ser Ser Pro     Asn Thr Ser Arg
        115                 120                     125 aca ttg act gcg ggg gcg gct acg tga agc tgt ttc cgg ccg gcc tgg    1750
Thr Leu Thr Ala Gly Ala Ala Thr     Ser Cys Phe Arg Pro Ala Trp
    130                 135 acc aga agg aca tgc acg ggg act ctg agt aca aca tca tgt ttg gtc    1798
Thr Arg Arg Thr Cys Thr Gly Thr Leu Ser Thr Thr Ser Cys Leu Val
                145                 150                 155 ctg aca tct gtg gcc ccg gca cca aga agg ttc acg tca tct tca act    1846
Leu Thr Ser Val Ala Pro Ala Pro Arg Arg Phe Thr Ser Ser Ser Thr
```

| | | |
|---|---|---|
| aca agg gca aga acg tgc tga tca aca agg aca tcc gtt gca agg acg<br>Thr Arg Ala Arg Thr Cys     Ser Thr Arg Thr Ser Val Ala Arg Thr<br>175             180                 185 | | 1894 |
| acg agt tca cac acc tgt aca cgc tga tcg tgc ggc cgg aca aca cgt<br>Thr Ser Ser His Thr Cys Thr Arg     Ser Cys Gly Arg Thr Thr Arg<br>190             195                 200 | | 1942 |
| atg agg tga aga ttg aca aca gcc agg tgg agt cgg gct ccc tgg agg<br>Met Arg     Arg Leu Thr Thr Ala Arg Trp Ser Arg Ala Pro Trp Arg<br>205             210                 215 | | 1990 |
| atg act ggg act tcc tac ccc cca aga aga taa agg acc cag atg cct<br>Met Thr Gly Thr Ser Tyr Pro Pro Arg Arg     Arg Thr Gln Met Pro<br>220             225                 230 | | 2038 |
| cga agc ctg aag act ggg acg agc ggg cca aga tcg acg acc cca cgg<br>Arg Ser Leu Lys Thr Gly Thr Ser Gly Pro Arg Ser Thr Thr Pro Arg<br>235             240             245             250 | | 2086 |
| act cca agc ccg agg act ggg aca agc ccg agc aca tcc ccg acc cgg<br>Thr Pro Ser Pro Arg Thr Gly Thr Ser Pro Ser Thr Ser Pro Thr Arg<br>            255             260             265 | | 2134 |
| acg cga aga agc ccg aag act ggg acg aag aaa tgg acg gag agt ggg<br>Thr Arg Arg Ser Pro Lys Thr Gly Thr Lys Lys Trp Thr Glu Ser Gly<br>            270             275             280 | | 2182 |
| agc cgc cgg tga ttc aga acc ccg agt aca agg gtg agt gga agc cgc<br>Ser Arg Arg     Phe Arg Thr Pro Ser Thr Arg Val Ser Gly Ser Arg<br>            285             290             295 | | 2230 |
| ggc aga tcg aca acc ccg att aca aag gca cct gga tcc acc ccg aaa<br>Gly Arg Ser Thr Thr Pro Ile Thr Lys Ala Pro Gly Ser Thr Pro Lys<br>            300             305             310 | | 2278 |
| tcg aca acc ccg agt act cgc ccg acg cta aca tct atg cct acg aca<br>Ser Thr Thr Pro Ser Thr Arg Pro Thr Leu Thr Ser Met Pro Thr Thr<br>            315             320             325 | | 2326 |
| gct ttg ccg tgc tgg gct tgg acc tct ggc agg tca agt cgg gca cca<br>Ala Leu Pro Cys Trp Ala Trp Thr Ser Gly Arg Ser Ser Arg Ala Pro<br>330             335             340             345 | | 2374 |
| tct tcg aca act tcc tca tca cca acg atg agg cgt acg cag agg agt<br>Ser Ser Thr Thr Ser Ser Ser Pro Thr Met Arg Arg Thr Gln Arg Ser<br>            350             355             360 | | 2422 |
| ttg gca acg aga cgt ggg gcg tca cca aga cgg ccg aga agc aga tga<br>Leu Ala Thr Arg Arg Gly Ala Ser Pro Arg Arg Pro Arg Ser Arg<br>            365             370             375 | | 2470 |
| aag aca agc agg acg agg agc agc gga tga agg agg agg agg aga<br>Lys Thr Ser Arg Thr Arg Ser Ser Gly     Arg Arg Arg Arg Arg<br>            380             385             390 | | 2518 |
| aga agc gga agg agg agg agg ccg agg agg acg agg agg aca agg<br>Arg Ser Gly Arg Arg Arg Arg Arg Pro Arg Arg Thr Arg Arg Thr Arg<br>            395             400             405 | | 2566 |
| acg aca agg agg acg agg atg agg acg agg agg aca agg acg agg agg<br>Thr Thr Arg Arg Thr Arg Met Arg Thr Arg Arg Thr Arg Thr Arg Arg<br>            410             415             420 | | 2614 |
| agg agg agg cgg ccg ccg gcc tcg agt acc cat atg atg ttc ctg act<br>Arg Arg Arg Arg Pro Pro Ala Ser Ser Thr His Met Met Phe Leu Thr<br>            425             430             435 | | 2662 |
| atg cta gac agg cca agg acg agc tgt ag<br>Met Leu Asp Arg Pro Arg Thr Ser Cys<br>440             445 | | 2691 |

<210> SEQ ID NO 13
<211> LENGTH: 123
<212> TYPE: PRT
<213> ORGANISM: Artificial

<220> FEATURE:
<223> OTHER INFORMATION: Synthetic Construct

<400> SEQUENCE: 13

```
Met Leu Leu Pro Val Pro Leu Leu Gly Leu Leu Gly Leu Ala Ala
1               5                   10                  15

Ala Glu Pro Val Val Tyr Phe Lys Glu Gln Phe Leu Asp Gly Asp Gly
                20                  25                  30

Trp Thr Glu Arg Trp Ile Glu Ser Lys His Lys Ser Asp Phe Gly Lys
            35                  40                  45

Phe Val Leu Ser Ser Gly Lys Phe Tyr Gly Asp Gln Glu Lys Asp Lys
        50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Pro Ala
                85                  90                  95

Arg Thr Pro Ala Ser Thr Pro Cys Arg Pro Asp Ser Ser Arg Ser Ala
                100                 105                 110

Thr Arg Ala Ser His Trp Trp Cys Ser Ser Pro
            115                 120
```

<210> SEQ ID NO 14
<211> LENGTH: 12
<212> TYPE: PRT
<213> ORGANISM: Artificial
<220> FEATURE:
<223> OTHER INFORMATION: Synthetic Construct

<400> SEQUENCE: 14

```
Asn Thr Ser Arg Thr Leu Thr Ala Gly Ala Ala Thr
1               5                   10
```

<210> SEQ ID NO 15
<211> LENGTH: 45
<212> TYPE: PRT
<213> ORGANISM: Artificial
<220> FEATURE:
<223> OTHER INFORMATION: Synthetic Construct

<400> SEQUENCE: 15

```
Ser Cys Phe Arg Pro Ala Trp Thr Arg Thr Cys Thr Gly Thr Leu
1               5                   10                  15

Ser Thr Thr Ser Cys Leu Val Leu Thr Ser Val Ala Pro Ala Pro Arg
                20                  25                  30

Arg Phe Thr Ser Ser Ser Thr Thr Arg Ala Arg Thr Cys
            35                  40                  45
```

<210> SEQ ID NO 16
<211> LENGTH: 17
<212> TYPE: PRT
<213> ORGANISM: Artificial
<220> FEATURE:
<223> OTHER INFORMATION: Synthetic Construct

<400> SEQUENCE: 16

```
Ser Thr Arg Thr Ser Val Ala Arg Thr Thr Ser Ser His Thr Cys Thr
1               5                   10                  15

Arg
```

<210> SEQ ID NO 17
<211> LENGTH: 9

-continued

<212> TYPE: PRT
<213> ORGANISM: Artificial
<220> FEATURE:
<223> OTHER INFORMATION: Synthetic Construct

<400> SEQUENCE: 17

Ser Cys Gly Arg Thr Thr Arg Met Arg
1               5

<210> SEQ ID NO 18
<211> LENGTH: 23
<212> TYPE: PRT
<213> ORGANISM: Artificial
<220> FEATURE:
<223> OTHER INFORMATION: Synthetic Construct

<400> SEQUENCE: 18

Arg Leu Thr Thr Ala Arg Trp Ser Arg Ala Pro Trp Arg Met Thr Gly
1               5                   10                  15

Thr Ser Tyr Pro Pro Arg Arg
            20

<210> SEQ ID NO 19
<211> LENGTH: 56
<212> TYPE: PRT
<213> ORGANISM: Artificial
<220> FEATURE:
<223> OTHER INFORMATION: Synthetic Construct

<400> SEQUENCE: 19

Arg Thr Gln Met Pro Arg Ser Leu Lys Thr Gly Ser Gly Pro Arg
1               5                   10                  15

Ser Thr Thr Pro Arg Thr Pro Ser Pro Arg Thr Gly Thr Ser Pro Ser
                20                  25                  30

Thr Ser Pro Thr Arg Thr Arg Arg Ser Pro Lys Thr Gly Thr Lys Lys
            35                  40                  45

Trp Thr Glu Ser Gly Ser Arg Arg
        50                  55

<210> SEQ ID NO 20
<211> LENGTH: 91
<212> TYPE: PRT
<213> ORGANISM: Artificial
<220> FEATURE:
<223> OTHER INFORMATION: Synthetic Construct

<400> SEQUENCE: 20

Phe Arg Thr Pro Ser Thr Arg Val Ser Gly Ser Arg Gly Arg Ser Thr
1               5                   10                  15

Thr Pro Ile Thr Lys Ala Pro Gly Ser Thr Pro Lys Ser Thr Thr Pro
            20                  25                  30

Ser Thr Arg Pro Thr Leu Thr Ser Met Pro Thr Thr Ala Leu Pro Cys
            35                  40                  45

Trp Ala Trp Thr Ser Gly Arg Ser Ser Arg Ala Pro Ser Ser Thr Thr
        50                  55                  60

Ser Ser Ser Pro Thr Met Arg Arg Thr Gln Arg Ser Leu Ala Thr Arg
65                  70                  75                  80

Arg Gly Ala Ser Pro Arg Pro Arg Ser Arg
                85                  90

<210> SEQ ID NO 21
<211> LENGTH: 9

```
<212> TYPE: PRT
<213> ORGANISM: Artificial
<220> FEATURE:
<223> OTHER INFORMATION: Synthetic Construct

<400> SEQUENCE: 21

Lys Thr Ser Arg Thr Arg Ser Ser Gly
1               5

<210> SEQ ID NO 22
<211> LENGTH: 63
<212> TYPE: PRT
<213> ORGANISM: Artificial
<220> FEATURE:
<223> OTHER INFORMATION: Synthetic Construct

<400> SEQUENCE: 22

Arg Arg Arg Arg Arg Arg Arg Ser Gly Arg Arg Arg Arg Pro Arg
1               5                   10                  15

Arg Thr Arg Arg Thr Arg Thr Arg Thr Arg Met Arg Thr Arg
                20                  25                  30

Arg Thr Arg Thr Arg Arg Arg Arg Arg Pro Pro Ala Ser Ser Thr
            35                  40                  45

His Met Met Phe Leu Thr Met Leu Asp Arg Pro Arg Thr Ser Cys
    50                  55                  60

<210> SEQ ID NO 23
<211> LENGTH: 418
<212> TYPE: PRT
<213> ORGANISM: Artificial
<220> FEATURE:
<223> OTHER INFORMATION: CRT peptide sequence from CRT cDNA

<400> SEQUENCE: 23

Met Leu Leu Pro Val Pro Leu Leu Gly Leu Leu Gly Leu Ala Ala
1               5                   10                  15

Ala Glu Pro Val Val Tyr Phe Lys Glu Gln Phe Leu Asp Gly Asp
                20                  25                  30

Trp Thr Glu Arg Trp Ile Glu Ser Lys His Lys Ser Asp Phe Gly Lys
            35                  40                  45

Phe Val Leu Ser Ser Gly Lys Phe Tyr Gly Asp Gln Glu Lys Asp Lys
    50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Phe Thr
                85                  90                  95

Val Lys His Glu Gln Asn Ile Asp Cys Gly Gly Gly Tyr Val Lys Leu
                100                 105                 110

Phe Pro Ala Gly Leu Asp Gln Lys Asp Met His Gly Asp Ser Glu Tyr
            115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
```

```
                195                 200                 205
Lys Asp Pro Asp Ala Ser Lys Pro Glu Asp Trp Asp Glu Arg Ala Lys
            210                 215                 220

Ile Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
            260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Ala Asn
290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Thr
            340                 345                 350

Ala Glu Lys Gln Met Lys Asp Lys Gln Asp Glu Glu Gln Arg Leu Lys
            355                 360                 365

Glu Glu Glu Glu Glu Lys Lys Arg Lys Glu Glu Glu Glu Ala Glu Glu
            370                 375                 380

Asp Glu Glu Asp Lys Asp Asp Lys Glu Asp Glu Asp Glu Asp Glu Glu
385                 390                 395                 400

Asp Lys Asp Glu Glu Glu Glu Ala Ala Ala Gly Gln Ala Lys Asp
                405                 410                 415

Glu Leu

<210> SEQ ID NO 24
<211> LENGTH: 430
<212> TYPE: PRT
<213> ORGANISM: Artificial
<220> FEATURE:
<223> OTHER INFORMATION: CRT peptide sequence with HA tag inserted into
      peptide
<220> FEATURE:
<221> NAME/KEY: MISC_FEATURE
<222> LOCATION: (413)..(424)
<223> OTHER INFORMATION: HA Tag

<400> SEQUENCE: 24

Met Leu Leu Pro Val Pro Leu Leu Gly Leu Leu Gly Leu Ala Ala
1               5                   10                  15

Ala Glu Pro Val Val Tyr Phe Lys Glu Gln Phe Leu Asp Gly Asp Gly
            20                  25                  30

Trp Thr Glu Arg Trp Ile Glu Ser Lys His Lys Ser Asp Phe Gly Lys
        35                  40                  45

Phe Val Leu Ser Ser Gly Lys Phe Tyr Gly Asp Gln Glu Lys Asp Lys
50                  55                  60

Gly Leu Gln Thr Ser Gln Asp Ala Arg Phe Tyr Ala Leu Ser Ala Arg
65                  70                  75                  80

Phe Glu Pro Phe Ser Asn Lys Gly Gln Pro Leu Val Val Gln Phe Thr
                85                  90                  95

Val Lys His Glu Gln Asn Ile Asp Cys Gly Gly Gly Tyr Val Lys Leu
            100                 105                 110
```

-continued

```
Phe Pro Ala Gly Leu Asp Gln Lys Asp Met His Gly Asp Ser Glu Tyr
        115                 120                 125

Asn Ile Met Phe Gly Pro Asp Ile Cys Gly Pro Gly Thr Lys Lys Val
    130                 135                 140

His Val Ile Phe Asn Tyr Lys Gly Lys Asn Val Leu Ile Asn Lys Asp
145                 150                 155                 160

Ile Arg Cys Lys Asp Asp Glu Phe Thr His Leu Tyr Thr Leu Ile Val
                165                 170                 175

Arg Pro Asp Asn Thr Tyr Glu Val Lys Ile Asp Asn Ser Gln Val Glu
                180                 185                 190

Ser Gly Ser Leu Glu Asp Asp Trp Asp Phe Leu Pro Pro Lys Lys Ile
            195                 200                 205

Lys Asp Pro Asp Ala Ser Lys Pro Glu Asp Trp Asp Glu Arg Ala Lys
        210                 215                 220

Ile Asp Asp Pro Thr Asp Ser Lys Pro Glu Asp Trp Asp Lys Pro Glu
225                 230                 235                 240

His Ile Pro Asp Pro Asp Ala Lys Lys Pro Glu Asp Trp Asp Glu Glu
                245                 250                 255

Met Asp Gly Glu Trp Glu Pro Pro Val Ile Gln Asn Pro Glu Tyr Lys
                260                 265                 270

Gly Glu Trp Lys Pro Arg Gln Ile Asp Asn Pro Asp Tyr Lys Gly Thr
            275                 280                 285

Trp Ile His Pro Glu Ile Asp Asn Pro Glu Tyr Ser Pro Asp Ala Asn
    290                 295                 300

Ile Tyr Ala Tyr Asp Ser Phe Ala Val Leu Gly Leu Asp Leu Trp Gln
305                 310                 315                 320

Val Lys Ser Gly Thr Ile Phe Asp Asn Phe Leu Ile Thr Asn Asp Glu
                325                 330                 335

Ala Tyr Ala Glu Glu Phe Gly Asn Glu Thr Trp Gly Val Thr Lys Thr
                340                 345                 350

Ala Glu Lys Gln Met Lys Asp Lys Gln Asp Glu Glu Gln Arg Leu Lys
            355                 360                 365

Glu Glu Glu Glu Glu Lys Lys Arg Lys Glu Glu Glu Glu Ala Glu Glu
        370                 375                 380

Asp Glu Glu Asp Lys Asp Asp Lys Glu Asp Glu Asp Glu Asp Glu Glu
385                 390                 395                 400

Asp Lys Asp Glu Glu Glu Glu Ala Ala Ala Gly Leu Glu Tyr Pro
            405                 410                 415

Tyr Asp Val Pro Asp Tyr Ala Arg Gln Ala Lys Asp Glu Leu
        420                 425                 430
```